(12) United States Patent
Zumbrum

(10) Patent No.: US 8,613,422 B2
(45) Date of Patent: Dec. 24, 2013

(54) FLUID TRANSFER DEVICE

(75) Inventor: Michael A. Zumbrum, New Oxford, PA (US)

(73) Assignee: Allpure Technologies, Inc., New Oxford, PA (US)

( * ) Notice: Subject to any disclaimer, the term of this patent is extended or adjusted under 35 U.S.C. 154(b) by 532 days.

(21) Appl. No.: 13/054,743

(22) PCT Filed: Jul. 18, 2008

(86) PCT No.: PCT/US2008/070482
§ 371 (c)(1),
(2), (4) Date: Feb. 25, 2011

(87) PCT Pub. No.: WO2010/008395
PCT Pub. Date: Jan. 21, 2010

(65) Prior Publication Data
US 2011/0155258 A1    Jun. 30, 2011

(51) Int. Cl.
*F16L 29/00* (2006.01)
*G01N 1/10* (2006.01)

(52) U.S. Cl.
USPC ..................................... 251/149.8; 73/863.86

(58) Field of Classification Search
USPC .................. 251/144, 149.8, 335.2; 73/863.86
See application file for complete search history.

(56) References Cited

U.S. PATENT DOCUMENTS

| | | |
|---|---|---|
| 2,685,412 A | 8/1954 | Schell |
| 2,767,587 A | 10/1956 | Perkins |
| 2,859,932 A | 11/1958 | Mackal |
| 2,872,817 A | 2/1959 | Pitts |
| 2,994,224 A | 8/1961 | Brown |
| 3,276,447 A | 10/1966 | Hamilton et al. |

(Continued)

FOREIGN PATENT DOCUMENTS

| | | |
|---|---|---|
| DE | 2 161 702 A1 | 6/1973 |
| DE | 3 633 431 A1 | 4/1988 |

(Continued)

OTHER PUBLICATIONS

Lynx ST Connectors. Datasheet [online], Millipore Corporation, 2008. Retrieved from the Internet: www.millipore.com (4 pages).

(Continued)

*Primary Examiner* — John Fox
(74) *Attorney, Agent, or Firm* — Womble Carlyle Sandridge & Rice LLP; Jacob S. Wharton

(57) ABSTRACT

A device is provided for transferring fluid into or out of a tank and is particularly useful in transferring fluid in a substantially aseptic, hygienic, or sterile manner. The device has a body with an elongate passage extending through the body. The body has a proximal end and a distal end. A longitudinally displaceable cannula is disposed in and extends along the passage in the body. A septum sealing the passage is at a first location; the septum being pierceable and self-sealing. A diaphragm sealing the passage is at a second location intermediate the septum and the distal end of the passage. The cannula extends through and is secured to the diaphragm and has a sharpened end disposed adjacent to or in the septum. Longitudinal displacement of the cannula causes its sharpened end to pierce and project through the septum, the diaphragm stretching to accommodate the displacement of the cannula while maintaining its aseptic seal of the passage.

30 Claims, 20 Drawing Sheets

(56) References Cited

U.S. PATENT DOCUMENTS

| | | | |
|---|---|---|---|
| 3,736,099 A | | 5/1973 | Begg et al. |
| 3,776,042 A | | 12/1973 | Werra et al. |
| 3,779,082 A | | 12/1973 | Galloway |
| 3,858,449 A | | 1/1975 | Singer |
| 4,018,059 A | | 4/1977 | Hatch |
| 4,056,981 A | * | 11/1977 | Kalka et al. ............... 73/863.85 |
| 4,244,224 A | | 1/1981 | Conn |
| 4,296,759 A | | 10/1981 | Joslin et al. |
| 4,479,393 A | | 10/1984 | Shores |
| 4,525,127 A | | 6/1985 | Welker |
| 4,527,436 A | | 7/1985 | Jones |
| 4,537,593 A | | 8/1985 | Alchas |
| 4,541,457 A | | 9/1985 | Blenkush |
| 4,557,151 A | | 12/1985 | Welker |
| 4,569,236 A | | 2/1986 | Kitchen et al. |
| 4,587,856 A | | 5/1986 | Otis |
| 4,622,457 A | | 11/1986 | Bradley et al. |
| 4,669,321 A | | 6/1987 | Meyer |
| 4,848,725 A | | 7/1989 | Tibbals, Jr. |
| 4,861,239 A | | 8/1989 | Simmons et al. |
| 4,941,517 A | | 7/1990 | Galloway |
| 5,031,841 A | * | 7/1991 | Schafer ........................ 239/584 |
| 5,158,558 A | | 10/1992 | Melker et al. |
| 5,246,204 A | * | 9/1993 | Ottung ........................ 251/331 |
| 5,360,413 A | | 11/1994 | Leason et al. |
| 5,463,908 A | | 11/1995 | Rosolia |
| 5,474,546 A | | 12/1995 | Ambrisco et al. |
| 5,535,635 A | | 7/1996 | Shaw |
| 5,839,715 A | * | 11/1998 | Leinsing ................... 251/149.1 |
| 5,868,433 A | | 2/1999 | Matkovich et al. |
| 6,032,543 A | | 3/2000 | Arthun et al. |
| 6,145,810 A | | 11/2000 | Connoly et al. |
| 6,221,041 B1 | | 4/2001 | Russo |
| 6,234,122 B1 | | 5/2001 | Kirschbaum et al. |
| 6,516,677 B1 | | 2/2003 | Suter |
| 6,558,365 B2 | | 5/2003 | Zinger et al. |
| 6,699,229 B2 | | 3/2004 | Zinger et al. |
| 6,715,624 B2 | | 4/2004 | Brockwell |
| 6,916,012 B2 | | 7/2005 | Newberg et al. |
| 6,994,315 B2 | * | 2/2006 | Ryan et al. ................. 251/149.6 |
| 7,272,981 B2 | | 9/2007 | Bigalke |
| 7,293,475 B2 | | 11/2007 | Furey et al. |
| 7,293,477 B2 | | 11/2007 | Furey et al. |
| 7,350,535 B2 | | 4/2008 | Liepold et al. |
| 7,578,205 B2 | | 8/2009 | Belongia et al. |
| 7,927,316 B2 | | 4/2011 | Prouix et al. |
| 8,408,078 B2 | * | 4/2013 | Mennenga et al. ........ 73/863.85 |
| 2006/0065868 A1 | | 3/2006 | Strong |
| 2006/0142730 A1 | | 6/2006 | Proulx et al. |
| 2007/0106264 A1 | | 5/2007 | Proulx et al. |
| 2008/0149877 A1 | | 6/2008 | Bessman |
| 2010/0133459 A1 | | 6/2010 | Zumbrum |
| 2011/0155258 A1 | | 6/2011 | Zumbrum |

FOREIGN PATENT DOCUMENTS

| | | |
|---|---|---|
| DE | 3 701 250 A1 | 7/1988 |
| DE | 6 980 7924 T2 | 1/2003 |
| EP | 0 103 396 A2 | 3/1984 |
| EP | 0 858 589 A1 | 8/1998 |
| EP | 0 858 589 B1 | 8/1998 |
| EP | 1 329 210 A1 | 7/2003 |
| JP | 2001523525 A | 11/2001 |
| SE | 507448 C2 | 6/1998 |
| SU | 649954 A | 2/1979 |
| WO | WO 86/02450 A1 | 4/1986 |
| WO | WO 91/00215 A | 1/1991 |
| WO | WO 97/16715 A1 | 5/1997 |
| WO | WO 99/26580 A1 | 6/1999 |
| WO | WO 03/090843 A1 | 11/2003 |
| WO | WO 2008-042285 A2 | 4/2008 |
| WO | WO 2008-136720 A1 | 11/2008 |
| WO | WO 2010/008395 A1 | 1/2010 |
| WO | WO 2010/008395 A9 | 1/2010 |
| WO | WO 2010/008396 A2 | 1/2010 |
| WO | WO 2011088350 A2 | 7/2011 |
| WO | WO 2011088350 A3 | 11/2011 |

OTHER PUBLICATIONS

Guidelines for Using the Lynx ST Connector. Technical Brief [online], Millipore Corporation, 2008. Retrieved from the Internet: www.millipore.com (2 pages).

FluidLine Technology Corporation FLT Bleed / Sample Valve Maintenance, Nov. 10, 2008. Datasheet [online], Fluid Line Technology. Retrieved from the Internet: www.fluidlinetech.com (1 page).

Risk Free Connection of Sterilized Single-Use Fluid Path Assemblies to Stainless Steel SIP Systems with Lynx ST (Steam-To) Connectors [online], Millipore Corporation, 2008. Retrieved from the Internet: www.millipore.com (8 pages).

Pure-Flo Solutions, Pure-Flo Radial Seated Tank Bottom Diaphragm Valve. Datasheet [online], ITT Industries, 2001. (2 pages).

ITT Sample & Bleed Valves. Datasheet [online], ITT Corporation, 2006. Retrieved from the Internet: www.ittpureflo.com. (4 pages).

Greene, R. and R. D'Aquino, "Disposable equipment: A mainstay in bioprocessing," Chemical Engineering Progress, pp. 10-11 (Nov. 1, 2002).

Haughney, H. and H. Aranha, Disposable processing gains you a competitive edge: enhancing manufacturing capacity with disposable filters, connectors, and membrane chromatography, Biopharm International, p. 50 (Oct. 2003).

Haughney, H. and M. Cardona, Taking disposable processing to the next level: a recent innovation extends the cost, labor and safety benefits of disposable processing to critical clarification and prefiltration steps used in pharmaceutical manufacturing, Biopharm. Trends, pp. 20-22 (Jun. 2004).

Janetschek, R., "Capsule Filters & Disposable Sterile Processing Systems," Pharmaceutical Processing, p. 8 (Jan. 2001).

Tingley, S., "Plastic factory: disposable biopharmaceutical manufacturing takes a giant leap forward; disposable technologies are quickly beginning to change the face of pharmaceutical cleanroom facility design and economics. (Alternative Manufacturing). (part one of two in series) (related article: Identified Causes of Aseptic Processing Failures)," Clean Rooms, pp. 1-4 (Feb. 2003).

Tingley, S., "Plastic Factory, Part II: the final pieces of the disposable puzzle. (Alternative Manufacturing). (sterile transfer process systems)" Clean Rooms, pp. 1-3 (Jun. 2003).

Wendt, D., Disposable processing systems: how suppliers are meeting today's biotech challenges from fluid handling to filtration, Biopharm International, p. 18 (Jul. 2003).

"New quality of data for bioprocessing bags. (Application Area)." Pharmaceutical Processing. Retrieved from the Internet: <URL: http://www.accessmylibrary.com/coms2/summary_0286-25022745_ITM>, pp. 1-2 (Jan. 2002).

"Connecting the Sanitary Flange," Datasheet [online], Millipore Corporation, 2007 (pp. 1-2).

International Preliminary Report on Patentability (Appln. No. PCT/US2008/070482, filed Jul. 18, 2008) mailed Jan. 27, 2011, pp. 1-6.

International Preliminary Report on Patentability (Appln. No. PCT/US2008/070488, filed Jul. 18, 2008) mailed Jan. 27, 2011, pp. 1-6.

U.S. Appl. No. 60/375,747, filed Apr. 26, 2002.

U.S. Appl. No. 60/500,024, filed Sep. 4, 2003.

Written Opinion of the International Searching Authority (Appln. No. PCT/US2008/070482, filed Jul. 18, 2008) mailed Apr. 16, 2009.

DE 3 701 250 A1 (Carstensen, CA) Jul. 28, 1988 (abstract) [online] Thomson Derwent (2003). Retrieved from Delphion Derwent, Accession No. 1988-213571, pp. 1-2.

DE 3 633 431 A1 (Buhler, R) Apr. 14, 1988 (abstract) [online] Thomson Derwent (2003). Retrieved from Delphion Derwent, Accession No. 1988-106251, pp. 1-3.

DE 2161702 A1 (Heil, E.) Jun. 14, 1973 (abstract) [online] Thomson Innovation (2011). Retrieved from Thomson Innovation, pp. 1-2.

DE 69807924 T2 (Russo, A.) Jan. 9, 2003 (abstract) [online] Thomson Innovation (2011). Retrieved from Thomson Innovation, pp. 1-3.

JP 2001523525 A Nov. 27, 2001 (abstract) [online] Thomson Innovation (2011). Retrieved from Thomson Innovation, pp. 1-2.

(56) References Cited

OTHER PUBLICATIONS

SU 649954 A (Vinichenko VP) Feb. 28, 1979 (abstract) [online] 2007 Derwent Information Ltd. Accession No. 1979-83821B, 1 page.
SE 507448 C2 (Nils, A.) Jun. 8, 1998 (abstract) [online} Thomson Innovation (2011). Retrieved from Thomson Innovation, pp. 1-2.
International Preliminary Report on Patentability for PCT/US2011/021341 (PCT app published as WO-2011/088350 A2) report issued Jul. 2012.
ITT Dualrange Control Valve. Datasheet [online], Pure-Flo, Retrieved from the Internet: www.ittpureflo.com (2 pages); date unknown, believed to be at least as early as Jul. 18, 2008.
Sanitary Inline Bleed and Sample Valves Datasheet [online], Fluid Line Technology. Retrieved from the Internet: www.fluidlinetech.com (1 page); date unknown, believed to be at least as early as Jul. 18, 2008.
Colder Products—Quick Couplings & Fittings for Industrial Applications. Retrieved from the Internet: <URL: http://www.colder.com/Markets/Industrial/IndustrialProducts/tabid/821/Default.aspx?ProductID=23> (1 page); date unknown, believed to be at least as early as Jul. 18, 2008.
Sanitary Inline Bleed and Sample Valves. Datasheet [online]. Fluid Line Technology Corporation. Retrieved from the Internet: www.fluidlinetech.com (1 page); date unknown, believed to be at least as early as Jul. 18, 2008.
Casella Sales & Marketing Inc., CSMI Sample Valves, Datasheet [online]. Retrieved from the Internet: www.casellasales.com (2 pages); date unknown, believed to be at least as early as Jul. 18, 2008.
Colder Products—Quick Couplings & Fittings for Industrial Applications—Industrial Products. Retrieved from the Internet: <URL: http://www.colder.com/Markets/Industrial/IndustrialProducts/tabid/821/Default.aspx?ProductID=22> (1 page); date unknown, believed to be at least as early as Jul. 18, 2008.
"Rapid Aseptic Fluid Transfer Introduction" Stedim Biosystems. [online]. Retrieved from the Internet: <URL: http: www.stedim.com/p2A_IDC_introduction.php> (2 pages); date unknown, believed to be at least as early as Jul. 18, 2008.
"Gore's Preliminary Invalidity Contentions to Plaintiff Millipore Corporation," (*Millipore Corporation* v. *W.L. Gore & Associates, Inc.*; Civil Action No. 09-10765 DPW) (108 pages). Oct. 29, 2009.
"Sip-Able Sample Valve," Datasheet [online]. Retrieved from the Internet: www.fluidlinetech.com (1 page); date unknown, believed to be at least as early as Jul. 18, 2008.

* cited by examiner

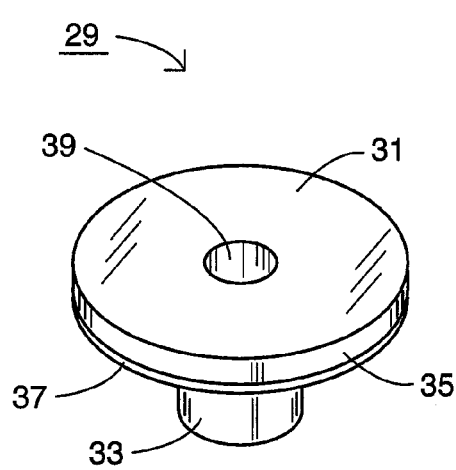 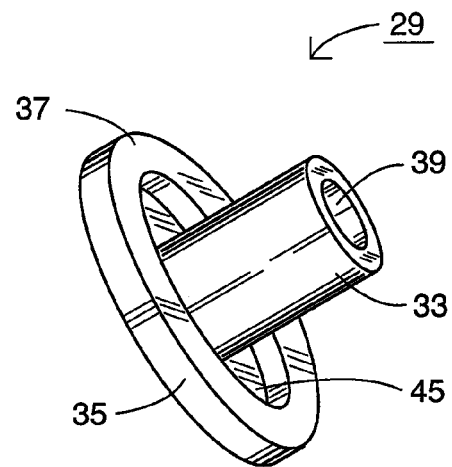
FIG. 9        FIG. 10
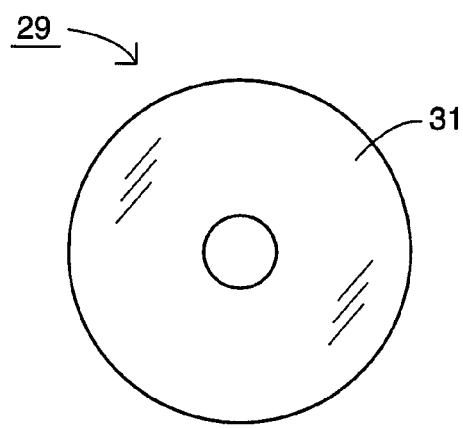 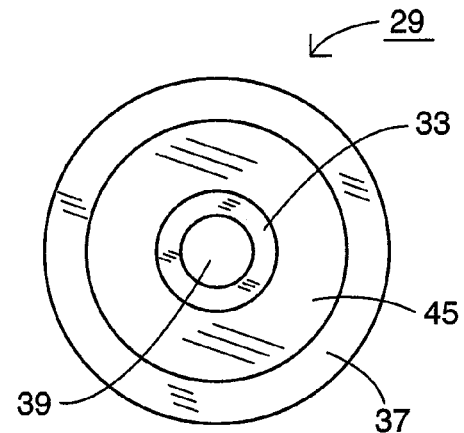
FIG. 11       FIG. 12

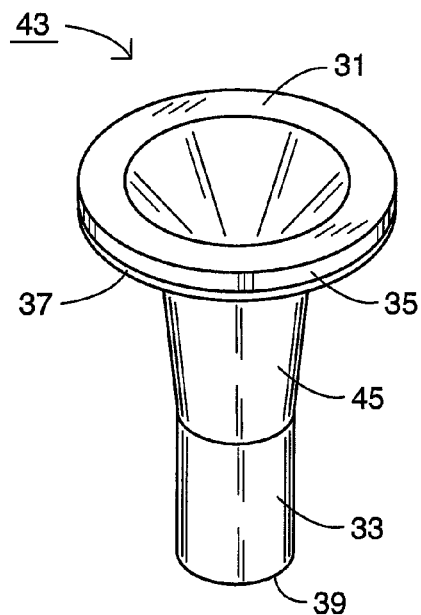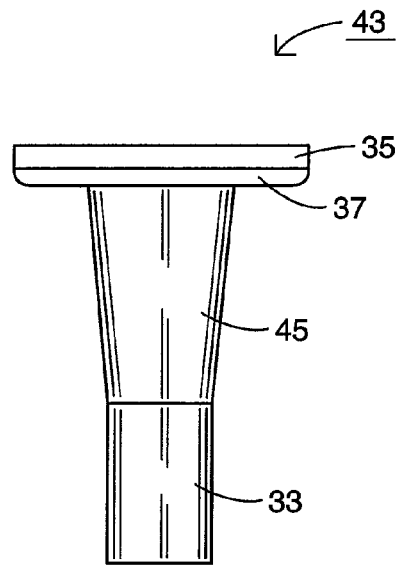
FIG.13    FIG.14
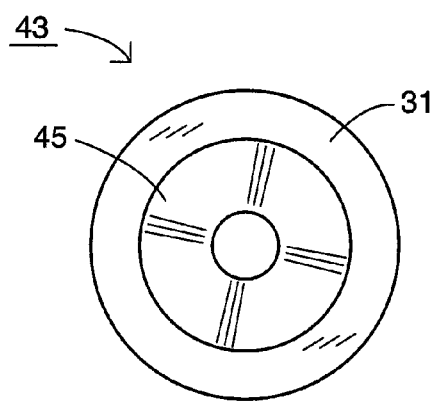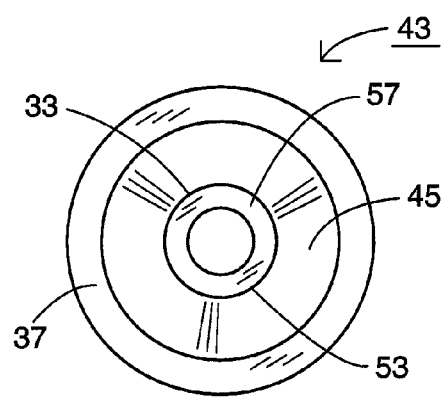
FIG.15    FIG.16

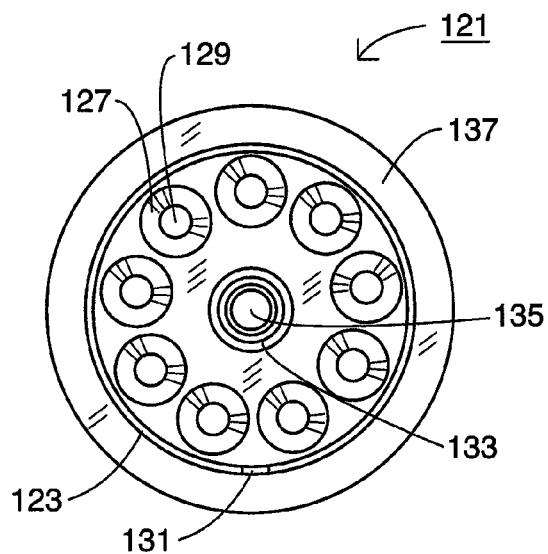
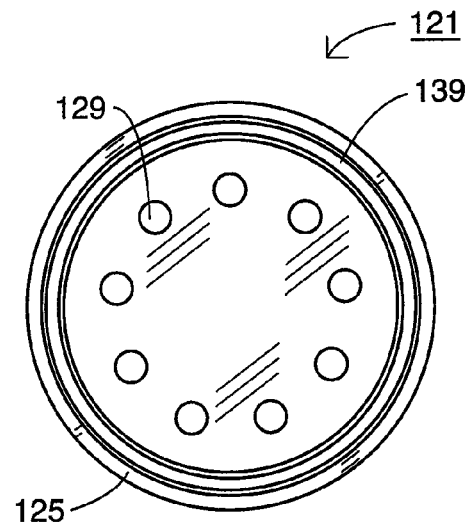
FIG. 41
FIG. 42
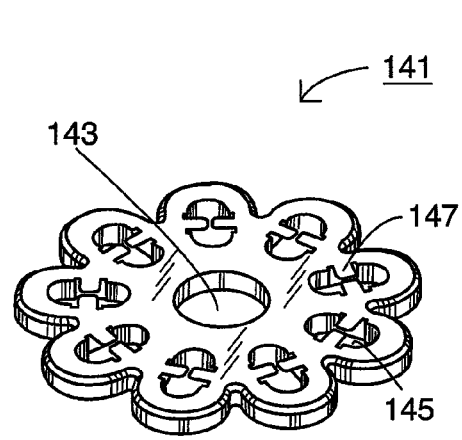
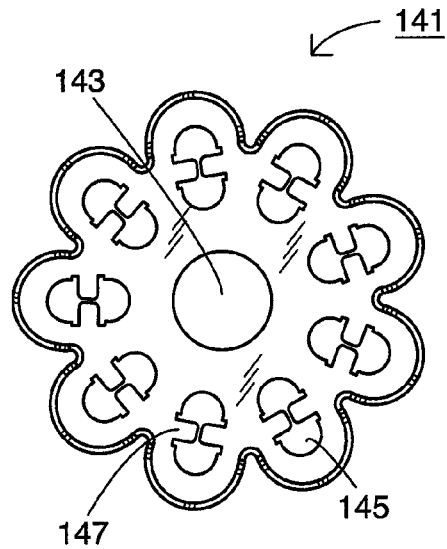
FIG. 43
FIG. 44

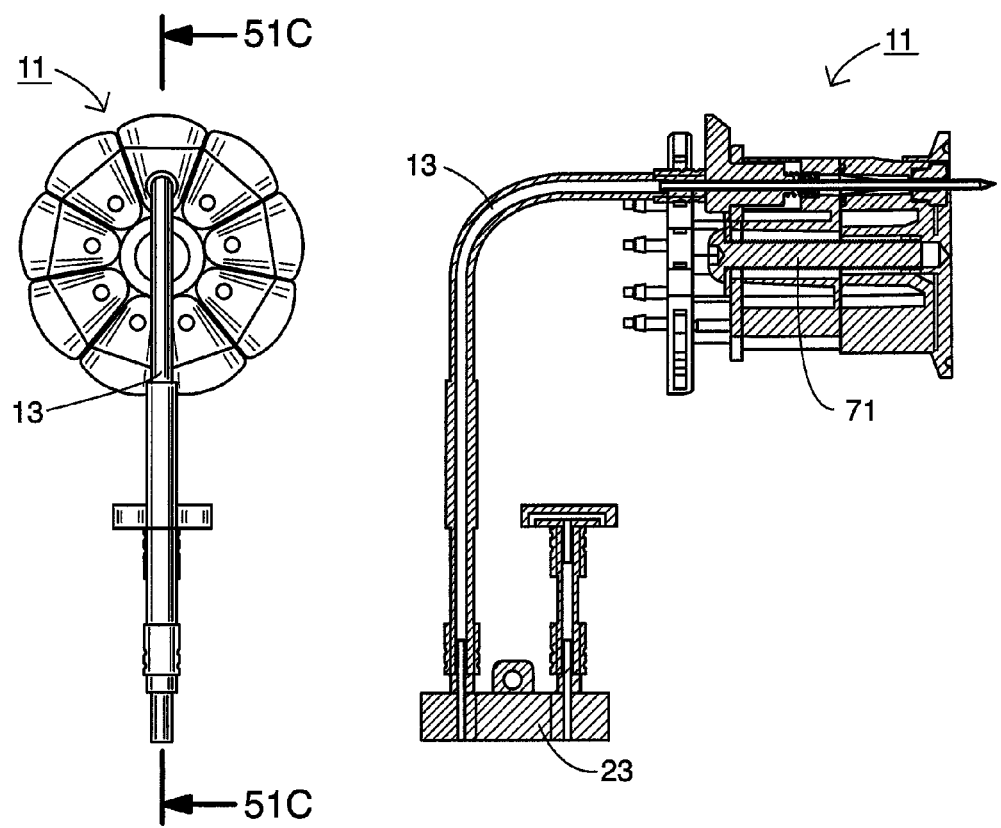
*FIG. 51B*  *FIG. 51C*

FLUID TRANSFER DEVICE

TECHNICAL FIELD

This disclosure relates generally to fluid transfer devices and more specifically to a fluid transfer device for transferring fluid in a substantially aseptic manner.

BACKGROUND

In the manufacturing and processing of many different products, it often is necessary to transfer fluid into or out of a closed processing system and do so in a substantially aseptic, hygienic, or sterile manner. In particular, the need to transfer fluid often arises in the manufacturing and processing of pharmaceuticals, biopharmaceuticals, or other biotechnology applications where processes are conducted in large process tanks, including but not limited to, the transfer of media solutions. The need for fluid transfer arises in other applications and industries as well, including but not limited to, the production of food, cosmetics, paint, chemicals, including hazardous chemicals, and the transfer and handling of semiconductor fluids. During transfers or sampling, fluid in tanks or other vessels must remain substantially free of contaminants. In addition, when making such transfers, it is desirable to keep the environment surrounding a vessel free from contamination by the contents of the vessel or a sample taken therefrom. It is often the case that throughout the manufacturing process there is a need to take multiple samples from the fluid or, in some circumstances, add additional fluid or media to the fluid in a vessel. To accomplish a substantially aseptic, hygienic, or sterile transfer, it is desirable to control the environment through which the fluid flows, for example, the pathway from a tank to a sample container should be substantially aseptic, hygienic, or sterile along the entire pathway. Furthermore, it is desirable that the fluid transfer device be safe for use, reliable, and of low-cost construction.

It is also desirable to transfer fluid using a device which is pre-sterilized and disposable. A pre-sterilized device avoids the need for an operator to prepare the device for use. In addition, a disposable device avoids the time consuming and laborious task of sterilizing sampling equipment.

In view of the above, there exists a need for a fluid transfer device that is pre-sterilized and disposable and capable of use in common industrial settings, such as those found in the pharmaceutical, biopharmaceutical, or other high purity industries.

SUMMARY

Briefly described, a fluid transfer device is disclosed for transferring fluid to or from a fluid receptacle, such as a tank, in a substantially aseptic manner. As used herein, the term "aseptic" includes aseptic, hygienic, or sterile conditions. The device comprises a body with an elongate passage extending through the body. The body has a proximal end and a distal end. The proximal end is that end closest to the vessel from which fluid is transferred. The distal end is that end furthest away from the vessel from which fluid is transferred. A longitudinally displaceable cannula is disposed in and extends along the passage in the body. A septum sealing the passage is at a first location; the septum being pierceable and self-sealing. A diaphragm sealing the passage is at a second location intermediate the septum and the distal end of the passage. The cannula extends through and is secured to the diaphragm and has a sharpened end disposed adjacent to or in the septum. Longitudinal displacement of the cannula towards the septum causes its sharpened end to pierce and project through the septum, with the diaphragm stretching to accommodate the displacement of the cannula while maintaining its seal about the cannula and thus maintaining the seal of the passage. In a preferred embodiment, the passage between the septum and diaphragm is substantially aseptic. In another preferred embodiment, the entire pathway that fluid flows from the fluid vessel to a sample container is also substantially aseptic.

In yet another embodiment, the device also comprises a tank mount. In this embodiment, the tank mount is attached to the fluid transfer device. In other embodiments, the tank mount is substantially aseptic to meet the needs of the end user. In another embodiment, the tank mount contains an opening through which the cannula passes when the cannula is longitudinally displaced. In another embodiment, a groove is located in the tank mount and a seal is located in the groove that allows the formation of a seal between a tank mount and a tank. In yet another embodiment, the tank mount further comprises a threaded stud for mounting the fluid transfer device to a tank.

In another embodiment, the proximal end of the cannula is disposed in the septum prior to displacement. In another embodiment, the septum is constructed of a silicone elastomer. In yet another embodiment, the diaphragm is constructed of a silicone elastomer. In another embodiment, the diaphragm is constructed of a solvent resistant elastomer. In another embodiment, the septum is constructed of a solvent resistant elastomer. In another embodiment, the septum is constructed of a perfluoropolyether elastomer. In another embodiment, the diaphragm is constructed of a perfluoropolyether elastomer.

In yet another embodiment, the fluid transfer device comprises a tab assembly to which the cannula is connected. In this embodiment, the tab assembly controls the displacement of the cannula through the passage. In another embodiment, the tab assembly further comprises a tab guide. In this embodiment, longitudinal displacement of the tab assembly displaces the tab guide through a portion of the passage. In another embodiment, the cannula is axially biased longitudinally to maintain the proximal end of the cannula disposed adjacent to or within the septum. In this embodiment, the bias retracts the cannula to substantially its original position or retracted non-actuated position after displacement. In another embodiment, the cannula is axially biased by a spring.

In another embodiment, the device comprises a retaining cap at the distal end of the body. In yet another embodiment, the device comprises a retaining cap comprising an opening through which the cannula and tab guide pass. In another embodiment, the retaining cap engages the distal end of the body and further comprises restraining means to allow the tab guide and the cannula to move through the retaining cap and stop at a predetermined position. In yet another embodiment, the restraining means comprises an axial channel extending along the tab guide and a detent extending from the opening in the retaining cap. In this embodiment, the detent extends from the opening in the retaining cap into the axial channel along the tab guide. The detent limits the longitudinal displacement of the tab guide in the distal direction and thus keeps the tab guide and entire tab assembly from coming out of the retaining cap.

In another embodiment, the body of the device comprises a substantially cylindrical outer portion, at least one alignment aperture, and seats for the diaphragm and septum. In yet another embodiment, a single fluid transfer device is joined together with additional fluid transfer devices as described in herein to form a cartridge having a plurality of bodies.

In yet another embodiment, the device further comprises a safety retention band preventing the cannula from longitudinal displacement until removal of the safety retention band. In another embodiment, the distal end of the cannula is barbed. In yet another embodiment, the distal end of the cannula is fitted with a luer.

Also provided is a fluid transfer device comprising a plurality of bodies as described herein joined together to form a cartridge. In a preferred embodiment, nine fluid transfer devices are joined to form a single cartridge. Each fluid transfer device may comprise a body comprising an elongate passage extending through the body and having a proximal end and a distal end; a longitudinally displaceable cannula disposed in and extending along the passage; a septum sealing the passage at a first location, the septum being pierceable and self-sealing; a diaphragm sealing the passage at a second location intermediate the septum and the distal end of the passage; the cannula extending through and being secured to the diaphragm and having a sharpened end disposed adjacent the septum; and wherein longitudinal displacement of the cannula towards the septum causes its sharpened end to pierce and project through the septum, the diaphragm stretching to accommodate the displacement of the cannula while maintaining a seal about the cannula and thus maintaining the seal of the passage.

Also provided is a kit for transferring fluid comprising a fluid transfer device as described herein. The fluid transfer device may comprise one or more bodies joined together, each body comprising an elongated passage extending through the body and having a proximal end and a distal end; a longitudinally displaceable cannula disposed in and extending along the passage; a septum sealing the passage at a first location, the septum being pierceable and self-sealing; a diaphragm sealing the passage at a second location intermediate the septum and the distal end of the passage; the cannula extending through and being secured to the diaphragm and having a sharpened end disposed adjacent the septum; wherein longitudinal displacement of the cannula causing its sharpened end to pierce and project through the septum, the diaphragm stretching to accommodate the displacement of the cannula while maintaining its seal about the cannula and thus maintaining the seal of the passage. The kit may also contain a tank mount, one or more lengths of flexible tubing, and a plurality of sample containers. In a preferred embodiment the kit is rendered substantially aseptic and packaged to maintain a substantially aseptic state before use.

The invention will be better understood and appreciated upon review of the detailed description set forth below when taken in conjunction with the accompanying drawing figures, described briefly below. According to common practice, the various features of the drawings may not be drawn to scale. Dimensions and relative sizes of various features and elements in the drawings may be shown enlarged or reduced to illustrate more clearly the embodiments of the invention.

BRIEF DESCRIPTION OF THE DRAWINGS

FIG. 9 is a perspective view of an embodiment of an unstretched diaphragm.

FIG. 10 is another perspective view of an embodiment of an unstretched diaphragm.

FIG. 11 is a top view of an embodiment of an unstretched diaphragm.

FIG. 12 is a bottom view of an embodiment of an unstretched diaphragm.

FIG. 13 is a perspective view of an embodiment of a stretched diaphragm.

FIG. 14 is a side view of an embodiment of a stretched diaphragm.

FIG. 15 is a top view of an embodiment of a stretched diaphragm.

FIG. 16 is a bottom view of an embodiment of a stretched diaphragm.

FIG. 41 is a top view of an embodiment of a tank mount also showing an alignment channel.

FIG. 42 is a bottom view of an embodiment of a tank mount.

FIG. 43 is a perspective view of an embodiment of a retaining cap.

FIG. 44 is a top view of an embodiment of a retaining cap.

FIG. 51A-51C show a fluid transfer device assembly with flexible tubing and a sample container attached wherein the fluid transfer device is actuated.

DETAILED DESCRIPTION

Figure 1:
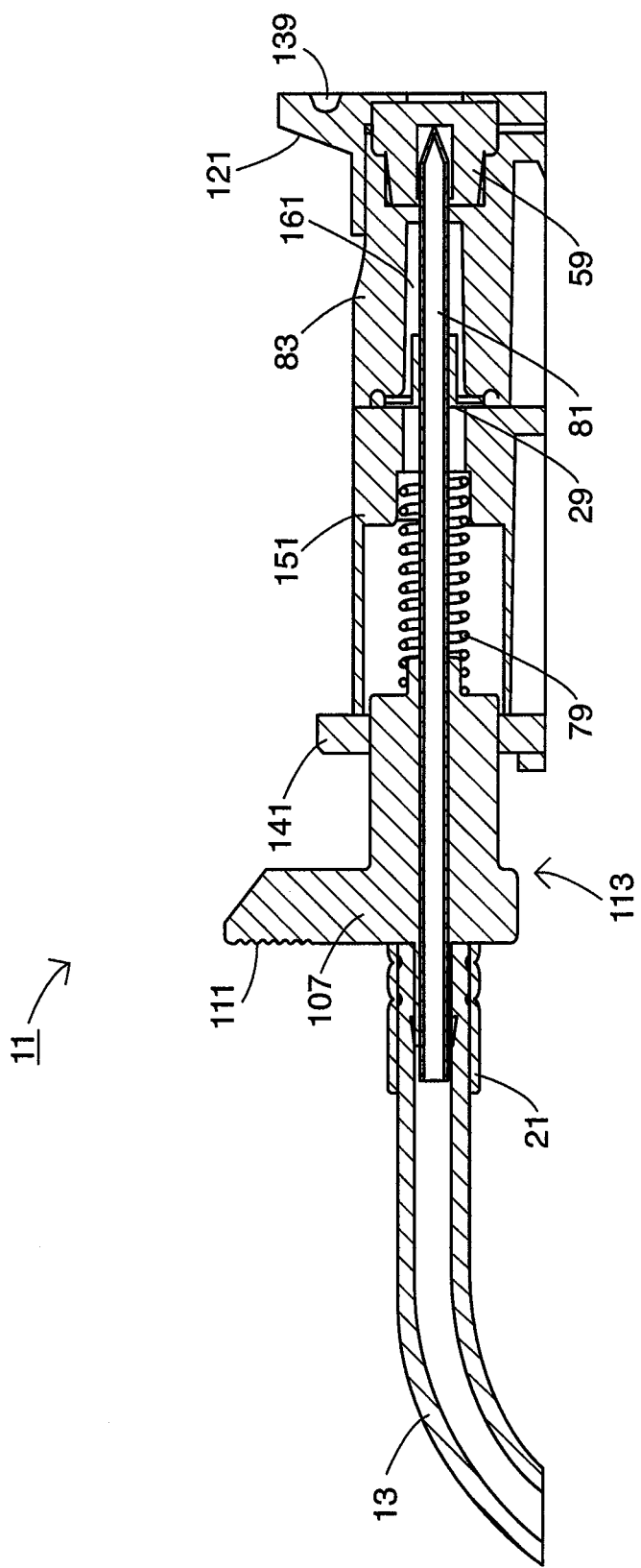
FIG. 1 is a cross-section of a fluid transfer device wherein the fluid transfer device is not actuated.

Referring now in more detail to the drawing figures, FIG. 1 is a cut-away or sectional view of a fluid transfer device 11. In this embodiment, the device may comprise flexible tubing 13, a crimped collar 21, a septum 59, a spring 79, a cannula 81, a lower portion of a body 83, a tab assembly 113, ridges 111 on a tab 107, a tank mount 121, a groove in the tank mount 139, a retaining cap 141, and an upper portion of a body 151.

Figure 2:
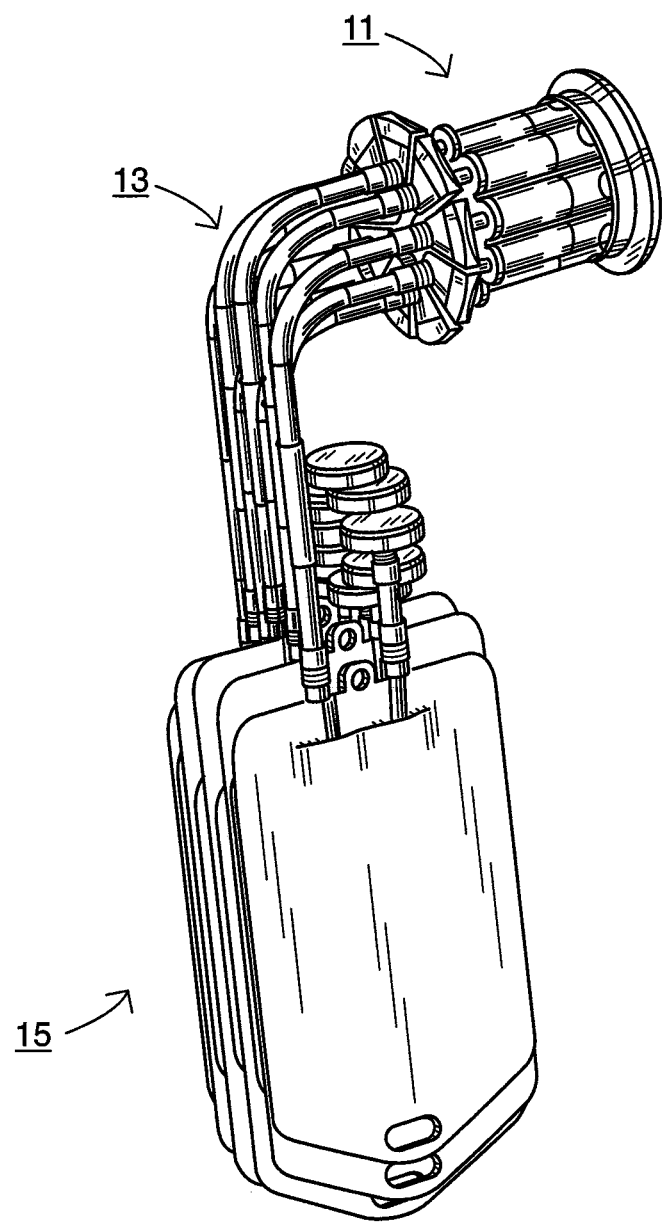
FIG. 2 is a perspective view of one embodiment of a fluid transfer device with flexible tubing and sample containers.

FIG. 2 is a perspective view of one embodiment of a fluid transfer device 11, flexible tubing 13, and sample containers 15 attached. The device may be used, for example, to take multiple fluid samples from a fluid receptacle, such as a tank, wherein a process is running. The samples may be taken simultaneously or over differing time intervals. The fluid transfer device 11 may be connected to a fluid receptacle, such as a tank, prior to a process being performed in the tank. The flexible tubing 13 may be connected to the fluid transfer device 11 prior to connecting to the fluid transfer device 11 to the tank. Likewise, the sample containers 15 may be connected to the flexible tubing 13 prior to connecting the flexible tubing 13 to the fluid transfer device 11 and before the fluid transfer device 11 is connected to a fluid receptacle, such as a tank. However, it is understood that the fluid transfer device 11, the flexible tubing 13, and the sample containers 15 may be attached in any order necessary to use the device to transfer fluid. In certain embodiments, the flexible tubing may be replaced in whole or part with rigid tubing. The device may be assembled and then rendered substantially aseptic, for example, by gamma irradiation.

Figure 3:
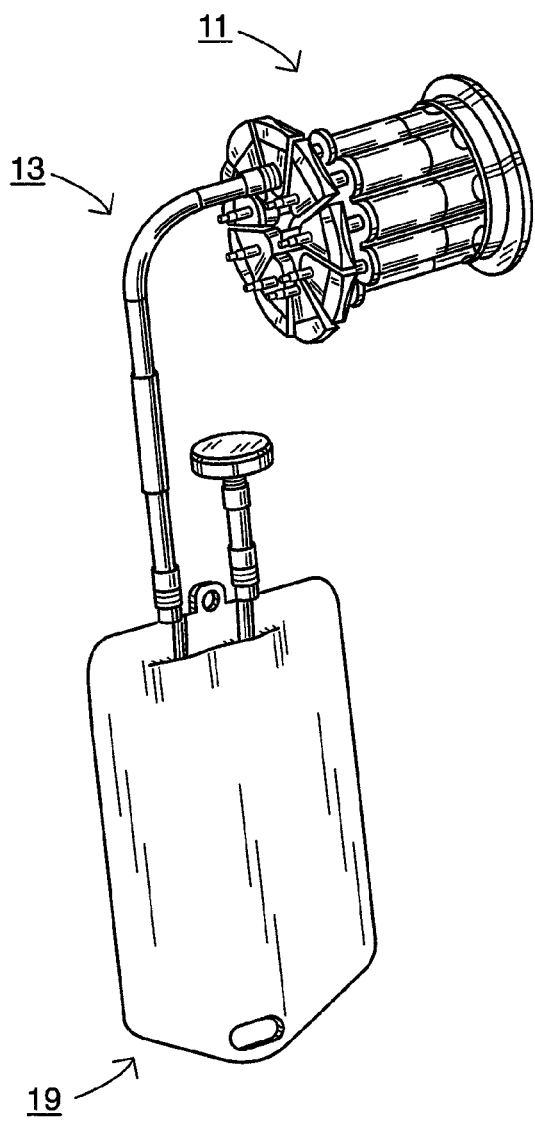
FIG. 3 is a perspective view of one embodiment of a fluid transfer device with a single flexible tube and sample container.

As shown in FIG. 3, the fluid transfer device 11 may be connected with a single fluid container 19 by way of flexible tubing 13. In fact any number of fluid containers less than the total possible may be connected. Fluid containers suitable for use with the fluid transfer device include without limitation, bags, bottles, syringes, other tanks, tubing, manifolds, or any combination thereof.

Figure 4:
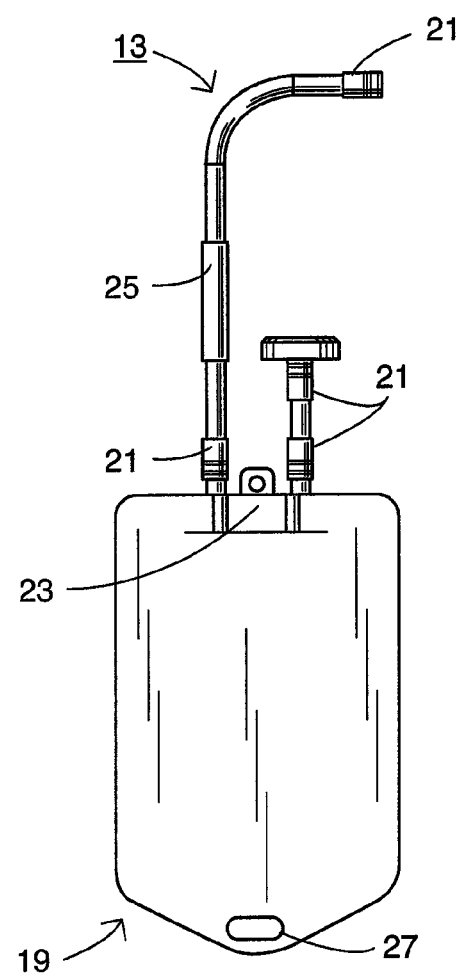
FIG. 4 depicts one embodiment of a sample container, flexible tubing, and individual elements of each.

As shown in FIG. 4, the flexible tubing 13 is connected to a sample container 19 by a crimped collar 21. Likewise, the flexible tubing 13 may be connected to a fluid transfer device 11, such as that depicted in FIG. 3, by a crimped collar 21. However, the flexible tubing 13 and the fluid transfer device 11 can be connected by other means, such as by press-fit, an adhesive, or the like. Likewise, the flexible tubing 13 can be connected to the sample container in similar means. In the illustrated embodiment, the sample container includes a bag insert 23 comprising two connectors. The bag insert 23 can be configured to accept a plurality of connections. In the embodiment shown, a sleeve 25 surrounding the flexible tubing 13 also is shown.

Figure 5:
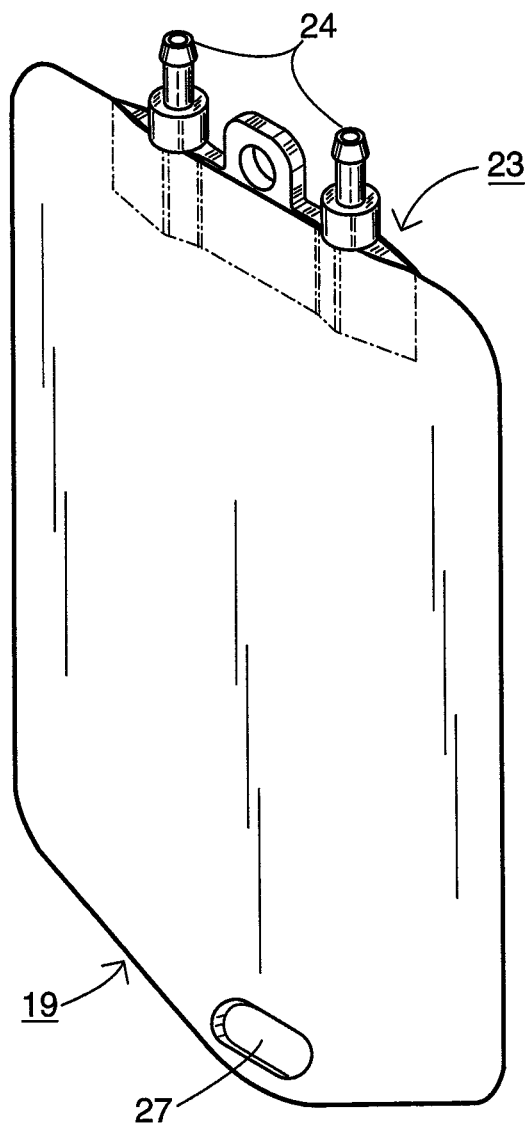
FIG. 5 is a perspective view of an embodiment of a sample container.

As shown in FIG. 5, an embodiment of the sample container 19 may comprise a thin bag that fills with fluid as a sample is taken. In the illustrated embodiment, the sample container 19 is shown with an opening 27 allowing the container to be hung, for example, on a hook. The sample container 19 is shown with a bag insert 23, as shown in detail in FIG. 8. In the embodiment shown, a connection 24 can be inserted into flexible tubing 13.

Figure 6:
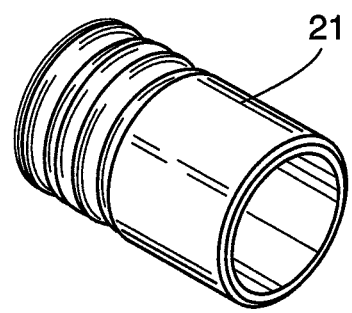
FIG. 6 is a perspective view of an embodiment of a crimped collar.
Figure 7:
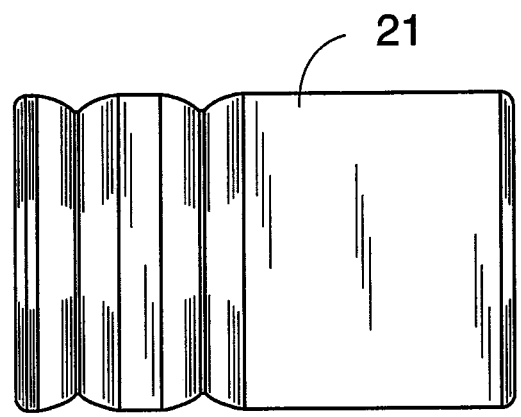
FIG. 7 is a side view of an embodiment of a crimped collar.

As shown in FIG. 6, a collar 21 is used to secure connections, such as between flexible tubing 13 and the fluid transfer device 11 (by way of the barbed connection on the tab discussed in more detail below). The collar 21 may be crimped to secure the connections using suitable tooling. In the embodiment illustrated in FIG. 6, the collar 21 is shown crimped. The collar 21 may also be used to connect the flexible tubing 13 to the sample container 19, such as shown in FIG. 4. FIG. 7 is a side view of the collar 21 in a crimped state.

Figure 8:
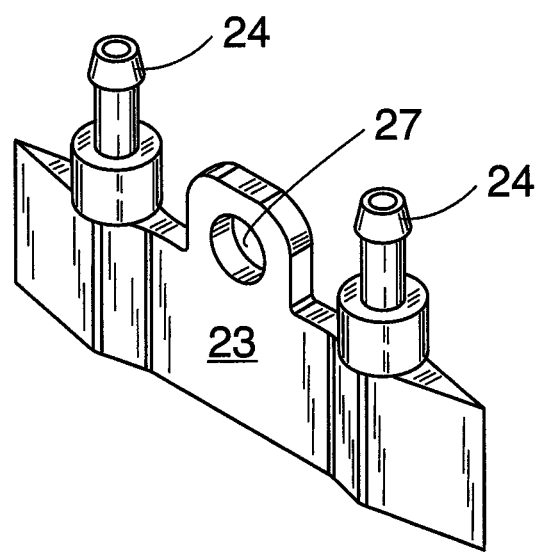
FIG. 8 is a perspective view of an embodiment of a bag insert.

As shown in FIG. 8, an embodiment of a bag insert 23 is provided. The bag insert 23 shown in FIG. 8 comprises two connections 24. In one embodiment, flexible tubing 13 (such as that shown in FIG. 4) is attached to one connection 24 and an air vent (not shown) may be connected to the other connection 24. However, it is understood that other attachments may be connected to connections 24, such as a luer injection site. In another embodiment, the bag insert 23 has one connection 24. In another embodiment the bag insert has more than two connections 24. As shown in the embodiment in FIG. 8, an opening 27 is provided in the bag insert 23 so that a sample container 19 containing bag insert 23 (as shown in FIG. 5) may be hung from, for example, a hook. In one embodiment, the bag insert 23 is attached to the sample container 19 by heat sealing.

Figure 46:
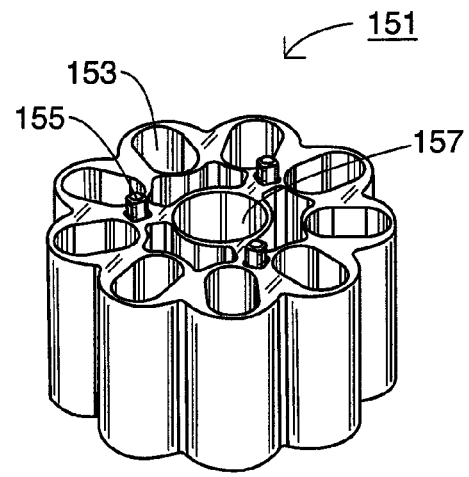
FIG. 46 is a perspective view of an embodiment of the upper portion of a body.

FIGS. 9, 10, 11 and 12 show various views of an embodiment of a diaphragm 29 for sealing around and holding the cannula 81 within the body 151 (as shown in FIG. 46). The diaphragm is made of flexible material and is capable of stretching in at least the direction of its axis. In this illustration, the diaphragm is shown in an un-stretched condition. The embodiment of the diaphragm 29 shown in FIG. 9 has a top face 31, a central body 33, a side 35, an annular bead 37, and a central opening 39. Another view of the embodiment of the diaphragm 29, is shown in FIG. 10. The diaphragm 29 shown in FIG. 10 has a central body 33, a side 35, an annular bead 37, a central opening 39, and a central membrane 45. In one embodiment, the central opening 39 is substantially cylindrical. In one embodiment, diaphragm 29 is constructed of silicone. In another embodiment, diaphragm 29 is constructed of a solvent resistant elastomer. In yet another embodiment, diaphragm 29 is constructed of a perfluoropolyether elastomer. However, it is understood diaphragm 29 may be constructed of any suitable material. As used in an embodiment of the fluid transfer device, a cannula (see FIG. 25) extends through the central opening 39 and is secured to the diaphragm 29 by molding, for example, the diaphragm 29 around the cannula when the diaphragm is produced. However, the diaphragm 29 may be secured to a cannula through other means such as with adhesives or sealants. It is further understood that the central opening 39 may have various shapes. FIG. 11 shows the top of one embodiment of a diaphragm, again in an unstretched state and, in particular, shows the top face 31 of the diaphragm. FIG. 12 depicts the bottom of one embodiment of a diaphragm 29 and, in particular, illustrates a central body 33, an annular bead 37, a central opening 39, and a central membrane 45.

FIG. 13 illustrates the diaphragm as it appears when stretched along its axis. A central membrane 45, now stretched, is again shown. Also shown are a top face 31, a side 35, an annular bead 37, and a central opening 39.

FIG. 14 is a side view of the stretched diaphragm 43.

FIG. 15 is a top view of the stretched diaphragm 43. Also shown is a top face 31 and a curved face of the stretched central membrane 45.

FIG. 16 is a bottom view of an embodiment of a stretched diaphragm 43. Also shown is a stretched central membrane 45, a central body 33, the exterior 53 of the central body 33, and the bottom 57 of the central body 33.

Figure 17:
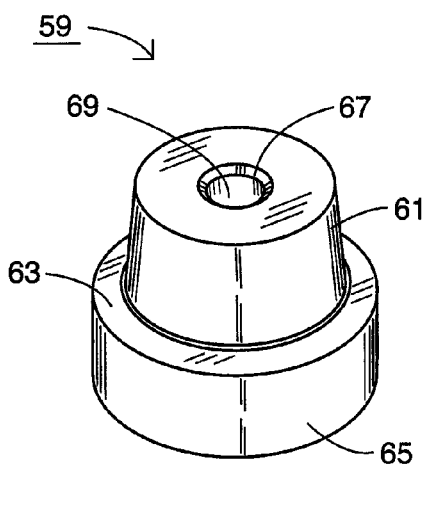
FIG. 17 is a perspective view of an embodiment of a septum.

FIG. 17 shows an embodiment of a septum 59 that is pierceable and self-sealing. The septum 59 has an angle insert wall 61, a rounded shoulder 63, a side 65, a rounded opening shoulder 67, and a central cavity 69. However, a septum that differs in configuration from septum 59 may be used provided that the septum forms an effective barrier in the fluid transfer pathway in a fluid transfer device. In one embodiment, septum 59 is constructed of silicone. In another embodiment, septum 59 is constructed of a solvent resistant elastomer. In yet another embodiment, septum 59 is constructed of a perfluoropolyether elastomer. However, it is understood that septum 59 may be constructed of any suitable material.

Figure 18:
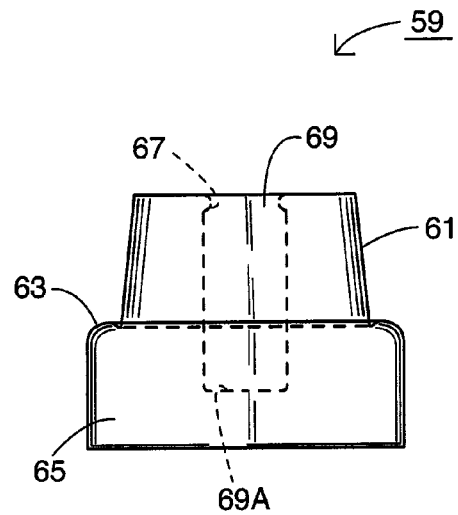
FIG. 18 is side view of an embodiment of a septum depicting the contours of the central cavity and rounded shoulder.

FIG. 18 is a side view of the septum 59 with interior surfaces shown in phantom line. The septum 59 had an angle insert wall 61, a rounded shoulder 63, a side 65, a rounded opening shoulder 67, a central cavity 69, and the base 69A of a central cavity 69. In one embodiment of the fluid transfer device, the sharpened end of a cannula (such as that depicted in FIG. 25) is disposed in the central cavity 69 but the tip of the cannula is not piercing the base 69A. In another embodiment of the fluid transfer device, the sharpened end of a cannula (such as that depicted in FIG. 25) is disposed in the central cavity 69 with its tip slightly piercing the base 69A but not penetrating the base. The base of the central cavity 69 is preferably constructed of material that, once pierced by the cannula and the cannula is retracted, will close forming a seal. Preferable materials for construction are listed above.

Figure 19:
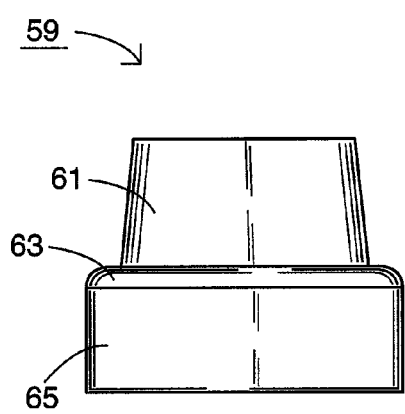
FIG. 19 is a side view of an embodiment of a septum.

FIG. 19 is another side view of the septum 59 is provided.

Figure 20:
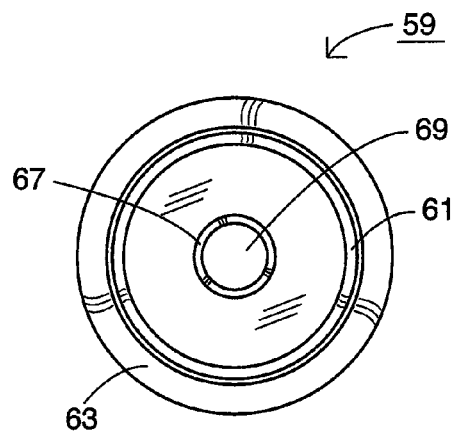
FIG. 20 is a top view of an embodiment of a septum.

FIG. 20 is a top view of the septum 59.

Figure 21:
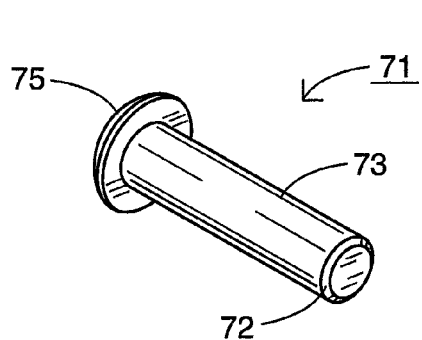
FIG. 21 is a perspective view of an embodiment of a bolt.
Figure 22:
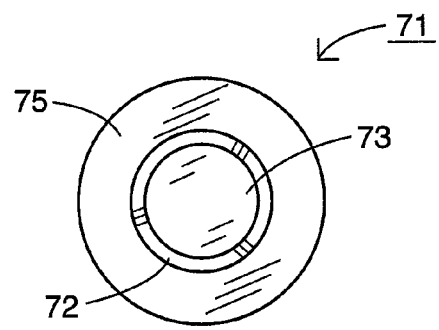
FIG. 22 is a bottom view of an embodiment of a bolt.
Figure 23:
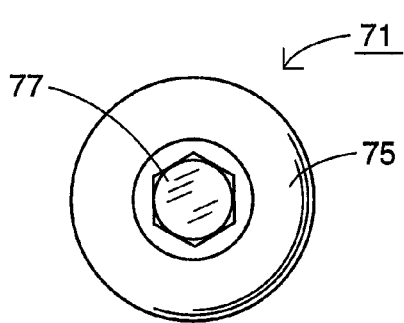
FIG. 23 is a top view of an embodiment of a bolt.

FIG. 21 shows an embodiment of a bolt 71, having a shaft 73, a head 75, and a tapered leading edge 72. The bolt is used to secure the fluid transfer device to a tank mount (see FIG. 39). As shown in FIG. 22, there is provided a bottom view of an embodiment of a bolt 71, a shaft 73, a head 75, and a tapered leading edge 72. FIG. 23 depicts a top view of an embodiment of a bolt 71, a head 75, and a drive shaft opening 77. The drive shaft opening 77 is configured for a hex driver. However, the draft shaft opening may be configured for any suitable driver. In one embodiment, the bolt 71 is threaded. In another embodiment, the bolt 71 is a shoulder bolt that controls compression of the sampling device to a fluid vessel.

Figure 24:
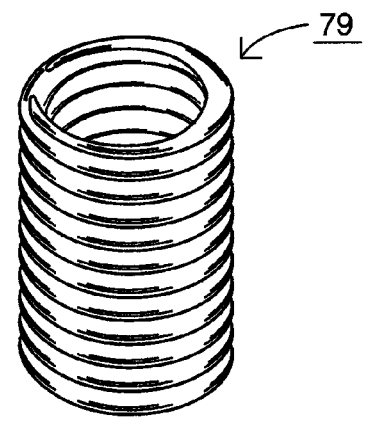
FIG. 24 is an embodiment of a compressed spring.

FIG. 24 shows a spring 79. As described in more detail below, a spring may be used to provide bias to a tab assembly and cannula. The bias forces the tab assembly and cannula (see FIG. 31) back to its original retracted non-actuated position or substantially thereabout. In a preferred embodiment, the bias forces the cannula back into the septum after fluid is transferred thus leaving the tip of the cannula disposed within the septum, for example, in the base 69A. In another embodiment, the bias leaves the tip of the cannula disposed within the central cavity 69. In either embodiment, the tip of the cannula is maintained within the sealed portion of the passage extending through the body.

Figure 25:
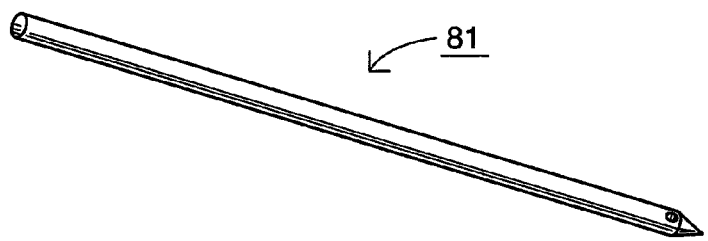
FIG. 25 is an embodiment of a cannula.
Figure 31:
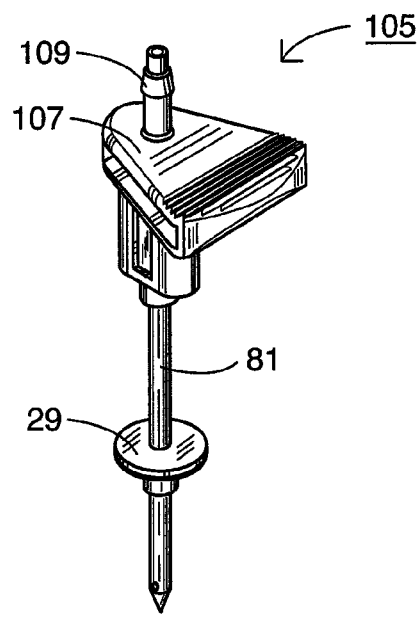
FIG. 31 is a perspective view of an embodiment of a tab assembly with a cannula and diaphragm.

FIG. 25 illustrates a cannula 81. In a preferred embodiment, the cannula 81 has a small circular opening in its tip to allow for the transfer of fluid. In another embodiment, the cannula is replaced by a hypodermic needle. In a preferred embodiment, the cannula is disposed in and extends along an elongate passage within the body of the fluid transfer device 11. In a preferred embodiment, the distal end of the cannula 81 is fitted with a luer (not shown). In another embodiment, the distal end of the cannula 81 is fitted with a barb. In a preferred embodiment, the cannula 81 extends through the tab assembly 113 as depicted in FIG. 31.

Figure 26:
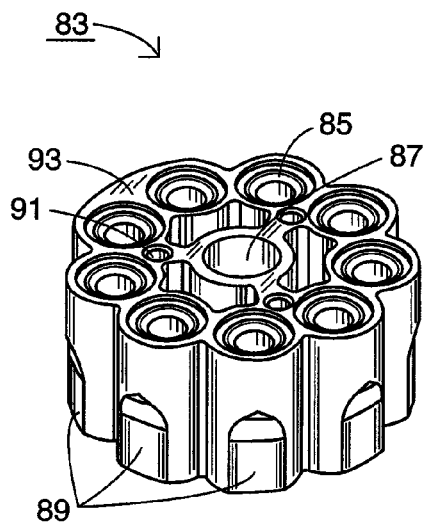
FIG. 26 is a perspective view of an embodiment of the lower portion of a body.
Figure 39:
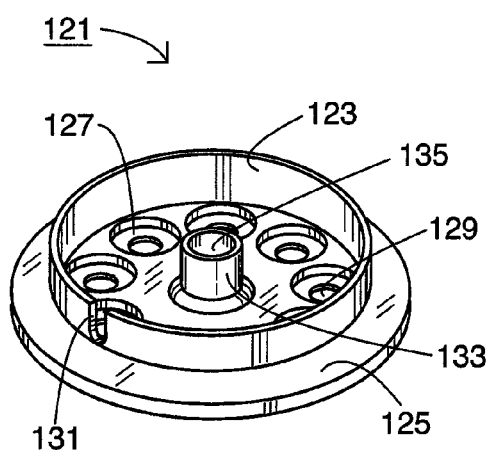
FIG. 39 is a perspective view of an embodiment of a tank mount showing an alignment channel.

FIG. 26 shows an embodiment of the lower portion of the body 83 of the fluid transfer device. In this embodiment, the lower portion of the body 83 is configured so that multiple fluid transfer devices are joined together. In the illustrated embodiment, a seat 85, comprising an annular groove, is provided where a diaphragm, such as the diaphragm 29 illustrated in FIG. 9, may be sealingly attached. Seat 85 may be configured with contours that match the annular bead 37 of diaphragm 29. The body 83 has a central opening 87, one or more alignment openings 91, and angled faces 89. The central opening 87 accommodates the bolt 71 when the fluid transfer device is attached to tank mount 121 (as shown in FIG. 39). The alignment openings 91 pair with alignment posts discussed in more detail below. In a preferred embodiment, the lower portion of the body 83 includes an extended face 93 that further includes an alignment key discussed in more detail below. The lower portion of the body 83 may be constructed out of any suitable material. In a preferred embodiment, the lower portion of the body 83 is constructed out of glass filled polyester. In another embodiment, the lower portion of the body 83 is constructed of polyvinylidene fluoride. In another embodiment, the lower portion of the body 83 is constructed out of polycarbonate which provides high temperature resistance. In another embodiment, the lower portion of the body 83 is constructed of polyether ether ketone (PEEK). In yet another embodiment the lower portion of the body 83 is constructed of Ultem® (polyetherimide).

Figure 27:
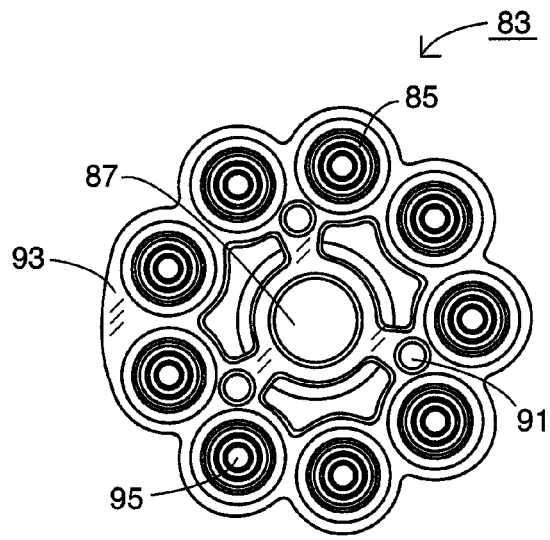
FIG. 27 is a top view of an embodiment of the lower portion of a body.

FIG. 27 illustrates an embodiment of a lower portion of the body 83, which may include a seat 85 that receives a diaphragm 29 (such as the one depicted in FIG. 9), a central opening 87, an alignment opening 91, an extended face 93, and a passage 95 extending through the lower body portion 83.

Figure 28:
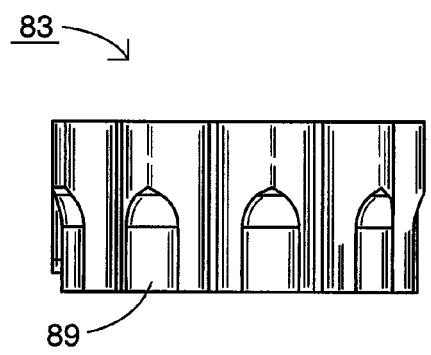
FIG. 28 is a side view of an embodiment of the lower portion of a body.
Figure 29:
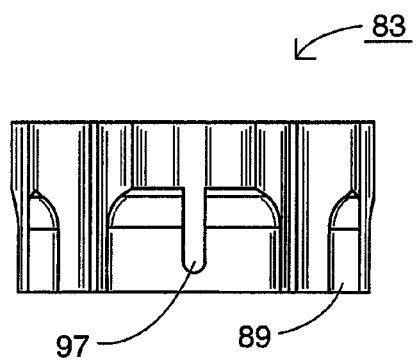
FIG. 29 is another side view of an embodiment of a holder showing an alignment key.

As shown in FIG. 28, the lower body portion of the body 83 may be formed with angled faces 89 to facilitate a fit with the tank mount (described below). The embodiment illustrated in FIG. 29 provides an extended face 93 and an alignment key 97 which corresponds to an alignment slot in the tank mount.

Figure 30:
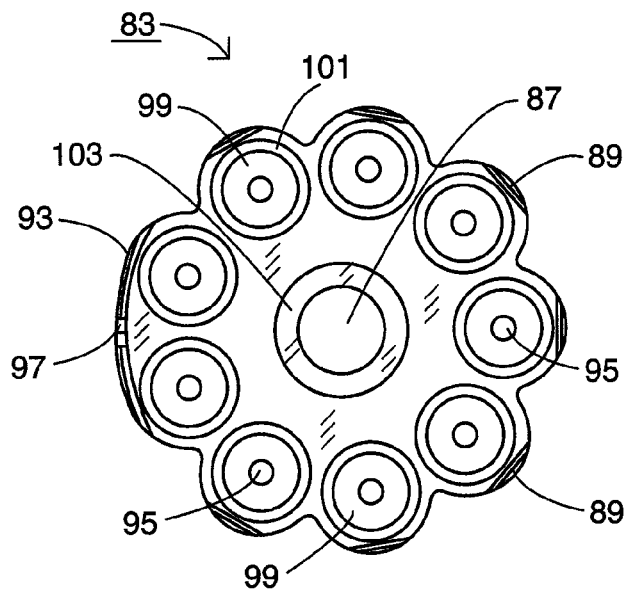
FIG. 30 is a bottom view of an embodiment of a holder.

FIG. 30 is a bottom view of an embodiment of a lower portion of a body 83 including a central opening 87, angled faces 89, an extended face 93, passages 95 through the body which also serve as alignment apertures to guide the cannula 81, an alignment key 97, septum recesses 99, a concave shoulder 101 within the septum recess 99, angled faces 89 that accommodate the tank mount 121, and a shoulder 103 to slide onto tank mount stud 133 (as shown in FIG. 39). In one embodiment, the septum recesses 99 are configured to receive septa (as depicted in FIGS. 17-20) with the rounded shoulder 63 of a septum mating with the concave shoulder 101 within the septum recess 99. In one embodiment, the septa are held in the septum recess 99 when the bolt 71 is secured to the tank mount (discussed below) thereby securing the tank mount to the lower portion of the body 83. In another embodiment, the septum is held in the septum recess 99 by silicone adhesive.

Figure 32:
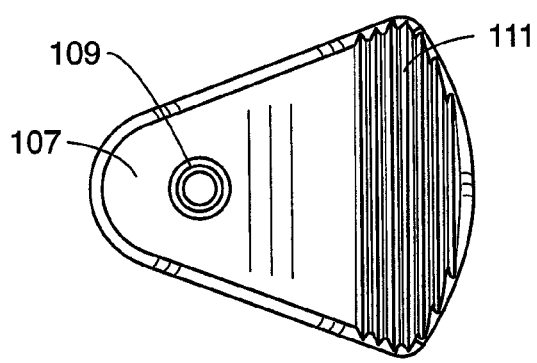
FIG. 32 is a top view of an embodiment of a tab assembly.
Figure 33:
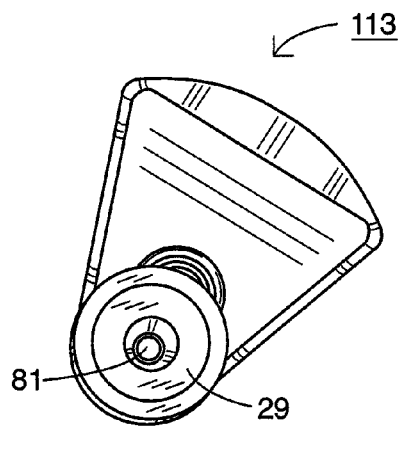
FIG. 33 is a bottom view of an embodiment of a tab assembly with a cannula and diaphragm.

FIG. 31 illustrates an embodiment of a cannula, a diaphragm, and tab assembly 105. A cannula 81 is shown to which an unstretched diaphragm 29 is secured. There also is provided a tab 107 and a barbed end 109 through which the cannula 81 may extend. FIG. 31 also depicts the cannula 81 extending through and secured to the diaphragm 29. In a preferred embodiment, diaphragm 29 is molded to cannula 81. As shown in FIG. 32, there is provided a top view of an embodiment of a tab 107, a barbed end 109, and ridges 111 that facilitate operation of the fluid transfer device. In one embodiment, tab assembly 113 is over-molded cannula 81. In the embodiment shown in FIG. 32, the ridges 111 provide a surface that an operator may depress to displace the cannula 81 longitudinally thereby moving the cannula from the fluid transfer device into a fluid vessel, such as a tank. FIG. 33 depicts a bottom view of an embodiment of a cannula and tab assembly 113, a diaphragm 29, and a cannula 81.

Figure 34:
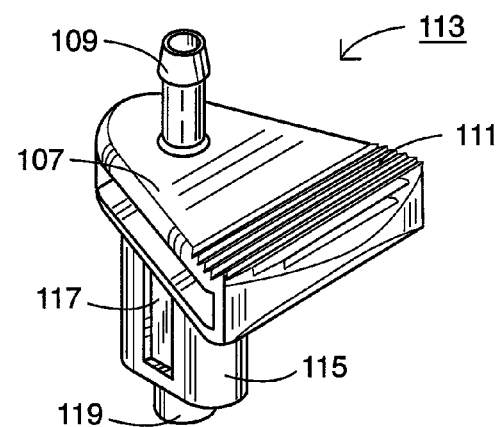
FIG. 34 is a perspective view of an embodiment of a tab and tab guide.
Figure 35:
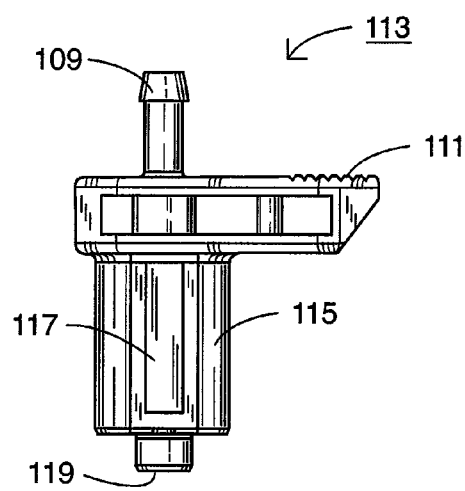
FIG. 35 is a side view of an embodiment of a tab and tab guide.

FIG. 34 shows a tab assembly 113 comprising a tab 107, a barb 109 (to which a cannula is fluidly connected from beneath and to which flexible tubing 13 may be connected from above), ridges 111 to facilitate operation as discussed above, a tab guide 115 to guide the tab during use, and an axial channel 117 in the tab guide 115. A cannula may be connected to the tab at the opening 119. Furthermore, a spring, such as that depicted in FIG. 24, may be fitted around the extension in which opening 119 is located. Such arrangement is depicted in detail in FIG. 1. As shown in FIG. 35, there is provided a side view of an embodiment of a tab assembly 113, a barb 109, ridges 111, a tab guide 115, an axial channel 117, and an opening 119 to which a cannula may be connected.

Figure 36:
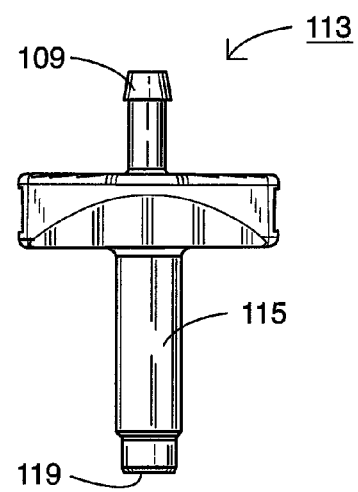
FIG. 36 is a rear view of an embodiment of a tab and tab guide.
Figure 37:
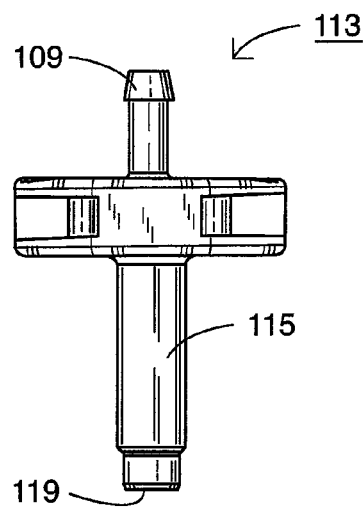
FIG. 37 is a front view of an embodiment of a tab and tab guide.
Figure 38:
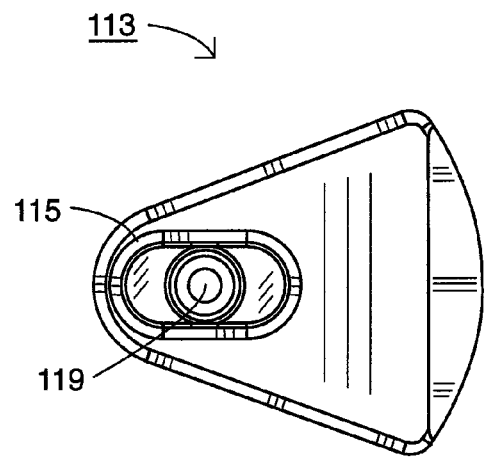
FIG. 38 is a bottom view of an embodiment of a tab and tab guide.

FIG. 36 illustrates a front view of an embodiment of a tab assembly 113, a barb 109, a tab guide 115, and an opening 119. Similarly, as shown in FIG. 37, there is provided a back view of an embodiment of a tab assembly 113, a barb 109, a tab guide 115, and an opening 119. As shown in FIG. 38, there is provided a bottom view of an embodiment of a tab assembly 113, a tab guide 115, and an opening 119.

Figure 40:
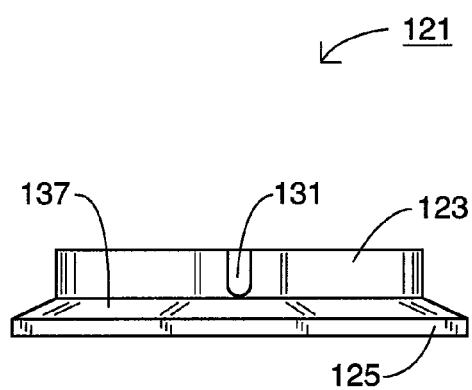
FIG. 40 is a side view of an embodiment of a tank mount showing an alignment channel.

FIG. 39 depicts an embodiment of a tank mount 121. Also provided is a wall 123, a plate 125, recesses 127 in the plate 125 for septa (such as those depicted in FIGS. 17-20), openings 129 in the recesses 127, an alignment slot 131 that receives the alignment key 97 (as shown, for example, in FIGS. 29 and 30), a threaded stud 133 in which an opening 135 is located. In one embodiment, threaded stud 133 is a female threaded stud. In one embodiment the threaded stud 133 receives a bolt, such as bolt 71 depicted in FIGS. 21, 22 and 23. As shown in FIG. 40, there is provided a side view of an embodiment of a tank mount 121. Also provided are a wall 123, a plate 125, and an alignment slot 131. FIG. 41 depicts top view of an embodiment of a tank mount 121 and provides a wall 123, an angled portion 137 of a plate 125, recesses 127, openings 129, an alignment slot 131, a threaded stud 133, and an opening 135 in the threaded stud 133. During actuation the tip of the cannula 81 passes through the openings 129 during actuation. FIG. 42 depicts a bottom view of an embodiment of a tank mount 121, and provides a plate 125, openings 129, and a groove 139. In one embodiment, a seal (not shown), such as an O-ring or hygienic gasket, is provided in the annular groove. Upon affixation to a tank (also not shown), a seal is formed between a fluid transfer device and a tank. The tank mount may be configured with one or more openings 129. In one embodiment, the tank mount 121 is substantially aseptic. The tank mount 121 may be constructed out of any suitable material. In one embodiment the tank mount is constructed out of titanium. In another embodiment the tank mount is constructed out of stainless steel.

Figure 45:
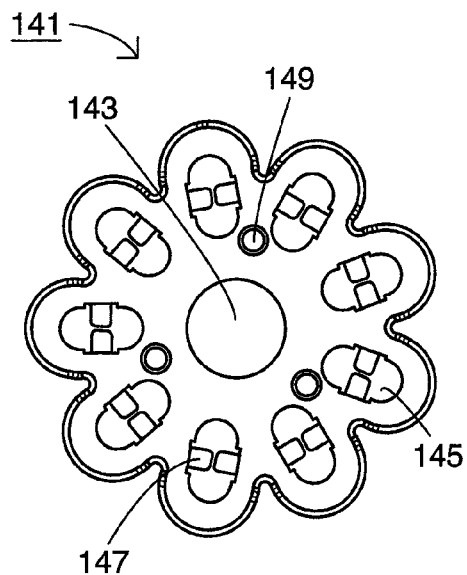
FIG. 45 is a bottom view of an embodiment of a retaining cap.

FIG. 43 shows a retaining cap 141, a central opening 143, and openings 145 through which tab guides, such as those depicted in FIGS. 34 and 35, pass, and detents 147. In the assembled fluid transfer device, the retaining cap 141 is located at the distal end of the upper portion of the body (discussed below). The retaining cap 141 may be constructed of a flexible material, such as polycarbonate or polyolefin. In a preferred embodiment, the retaining cap is constructed of polycarbonate. However, the retaining cap may be constructed from any suitable material. FIG. 44 depicts a top view of an embodiment of a retaining cap 141. FIG. 45 depicts a bottom view of a retaining cap 141, a central opening 143, openings 145, detents 147, and alignment openings 149. In a preferred embodiment, the detents 147 travel in the axial channel 117 of the tab guide 115. In one embodiment, the bottom surface of tab 107 contacts the top retaining cap 141, thereby limiting the axial travel of tab assembly 113 and compression of the interior components of fluid transfer device 11. When the tab 107 is retracted in a distal direction, the extended detents 147 keep the tab assembly 113 from coming out of the retaining cap 141 and potentially tearing the diaphragm and breaking the substantially aseptic state of the fluid transfer device and, in particular, the substantially aseptic state of the pathway through which fluid travels.

Figure 47:
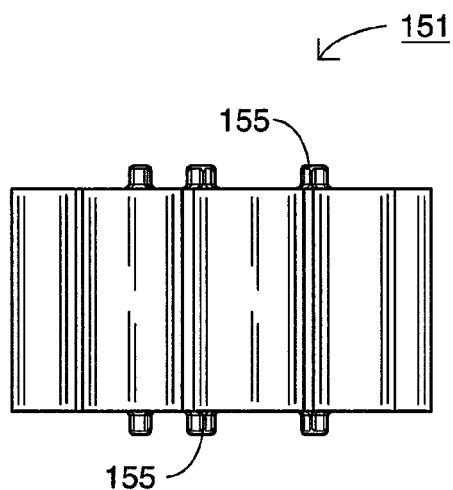
FIG. 47 is a side view of an embodiment of the upper portion of a body.
Figure 48:
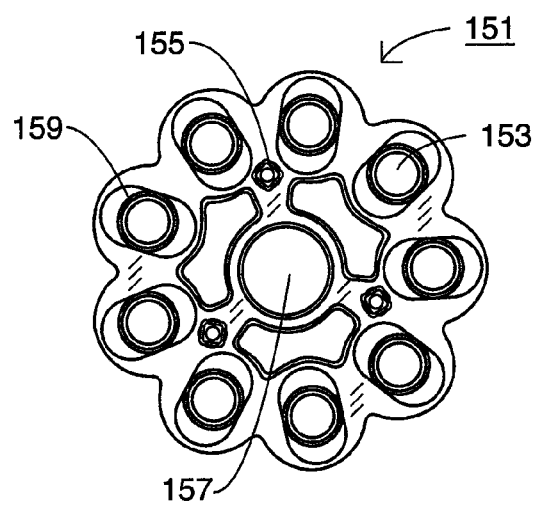
FIG. 48 is a top view of an embodiment of the upper portion of a body.
Figures 49, 50A:
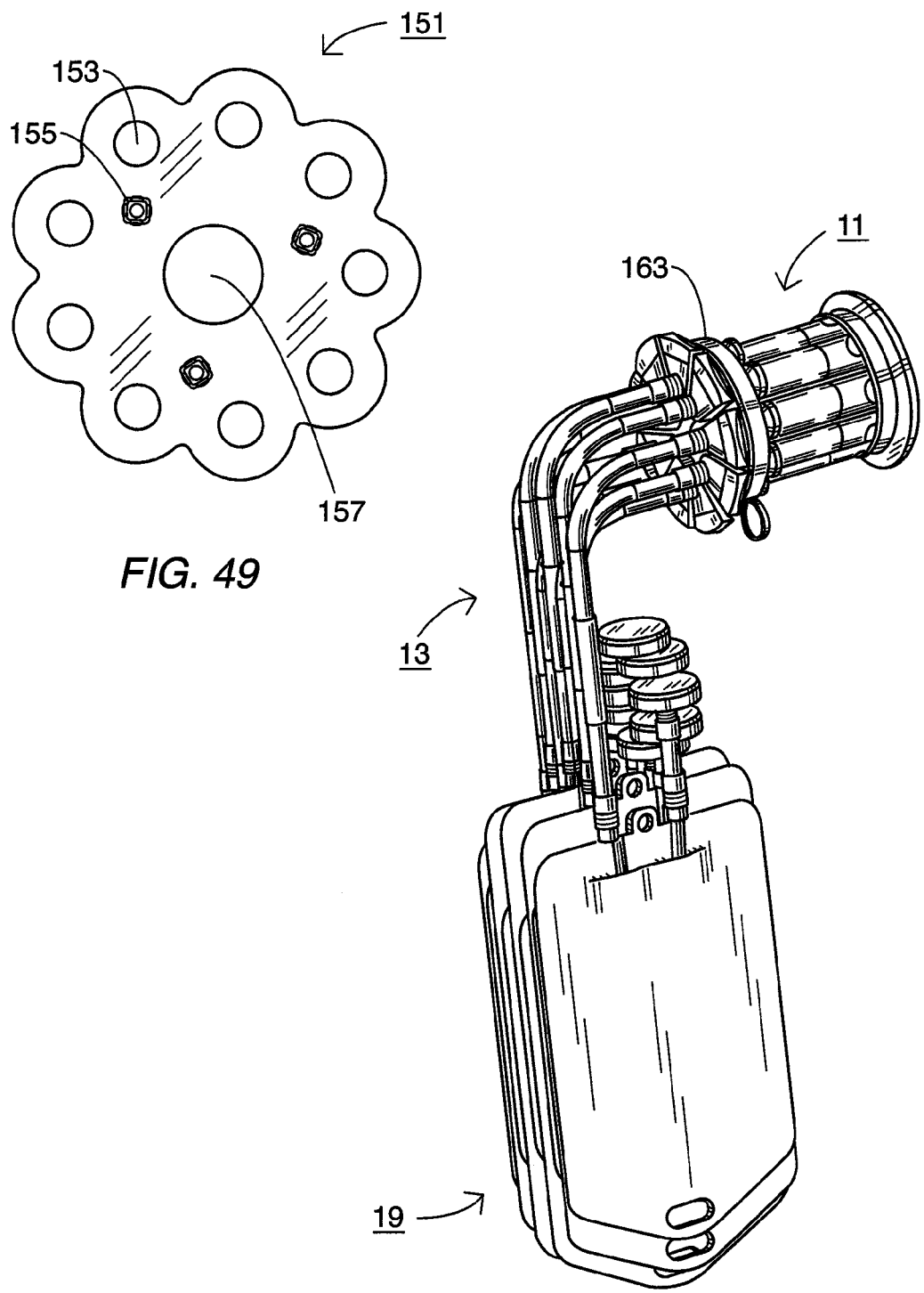
FIG. 49 is a bottom view of an embodiment of the upper portion of a body.
FIG. 50A-50C show a fluid transfer device assembly with flexible tubing and sample containers wherein the fluid transfer device is not actuated.

As shown in FIG. 46, an embodiment of an upper portion of the body 151 is provided along with openings 153 that extend through the upper portion of the body 151, alignment posts 155, and a central opening 157. The embodiment depicted in FIG. 47 provides a side view of one embodiment of an upper portion of the body 151 and provides for alignment posts 155 on both the top and bottom of the upper portion of the body 151. In one embodiment, when the fluid transfer device is assembled, the alignment posts 155 mate with the alignment openings 149 on the retaining cap 141 and the alignment openings 91 in the lower portion of the body 83. FIG. 48 depicts a top view of an embodiment of an upper portion of the body 151 and provides openings 153, alignment posts 155, a central opening 157, and annular shoulders 159 located in openings 153 in the upper portion of the body 151. In one embodiment, when the fluid transfer device is assembled, a spring, such as the one depicted in FIG. 24, is placed in the openings 153 and rests on the shoulders 159. When a tab and cannula assembly is placed in the openings 153, the spring provides bias, causing a tab that has been depressed to return to its original retracted non-actuated position or substantially thereabout. FIG. 49 depicts a bottom view of the upper portion of the body 151 and provides openings 153, and alignment posts 155.

The upper portion of the body 151, the lower portion of the body 83, and the retaining cap 141, as well as any other components made from thermoplastic materials may be joined by ultrasonic welding or by a thermoset adhesive.

Figure 50B:
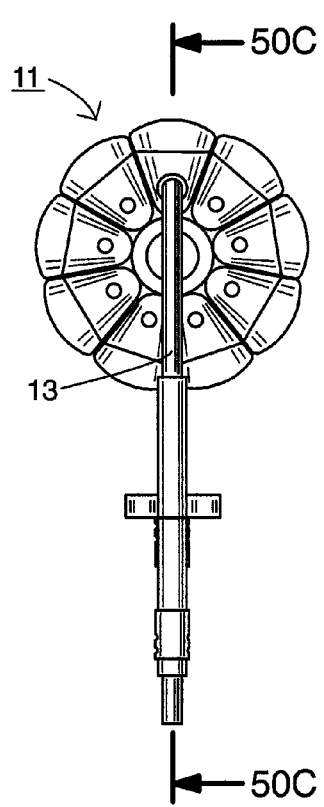
Figure 50C:
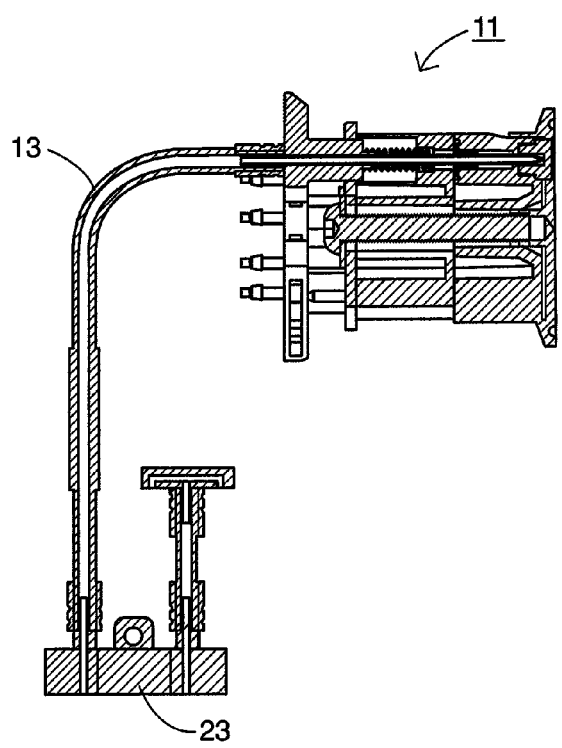

FIGS. 50A, 50B, and 50C illustrate an assembled fluid transfer device 11 prior to actuation; that is, the tabs shown on the fluid transfer device are in their original, rest, or retracted positions. The fluid transfer device may be used in a manner depicted in FIG. 50A wherein multiple sample containers are fluidly connected to the fluid transfer device by way of multiple pieces of flexible tubing 13. Also shown in FIG. 50A is safety retention band 163. Safety retention band 163 holds tabs 107 in place until operation and prevents unintentional longitudinal displacement of tabs 107. Safety retention band 163 is removed prior to use.

The fluid transfer device may also be used in a manner depicted in FIG. 50B, wherein only one sample container is connected by one piece of flexible tubing. FIG. 50B is a front view of a fluid transfer device 11 connected to flexible tubing 113.

In the embodiments shown in FIGS. 50A, 50B, and 50C, it is understood that the fluid transfer device contains multiple individual fluid transfer devices joined together to form a cartridge to facilitate multiple transfers. It is understood the fluid transfer device provided herein may be a single transfer device or joined together to provide for multiple transfer capabilities. In a preferred embodiment, the fluid transfer device comprises nine individual fluid transfer devices joined together, such as that depicted in FIGS. 50A and 50B.

FIG. 50C depicts a cross-section of an embodiment of a fluid transfer device. As illustrated, the fluid transfer device 11 is connected to flexible tubing which, in turn, is connected to a bag insert 23.

Referring back to FIG. 1, there is provided in cross-section a preferred embodiment of a fluid transfer device 11 and illustrates how the majority of the various components described above operate together. As illustrated in FIG. 1, the fluid transfer device is shown prior to usage, that is, with the cannula 81 in its original, rest, or retracted position. The fluid transfer device 11 comprises a tank mount 121 containing an annular groove 139. Also shown is the septum 59, a lower portion of the body 83, a diaphragm 29 (in an unstretched state), an upper portion of the body 151, a spring 79, a retaining cap 141, a tab assembly 113, ridges 111 on the tab 107, a collar 21, and flexible tubing 13. The passage 161 in the lower body portion 83 comprises an elongate passage extending through the body of the fluid transfer device 11. The elongated passage has a proximal end and a distal end. In a preferred embodiment passage 161 is substantially aseptic and sealed from the environment. In this preferred embodiment, the cannula 81 is disposed in and is longitudinally displaceable along the elongate passage with the tip of the cannula 81 disposed in the central cavity of the septum 59. As illustrated, a septum 59 seals the elongate passage at a proximal location. The septum 59 is both pierceable and self-sealing. Also illustrated is a diaphragm 29 that seals the elongate passage at a second, more distal location, from the septum 59. In this preferred embodiment, the portion of the elongate passage between the septum 59 and the diaphragm 29, and labeled as 161, is substantially aseptic. FIG. 31 also depicts the cannula 81 extending through and being secured to the diaphragm 29.

Figure 51A:
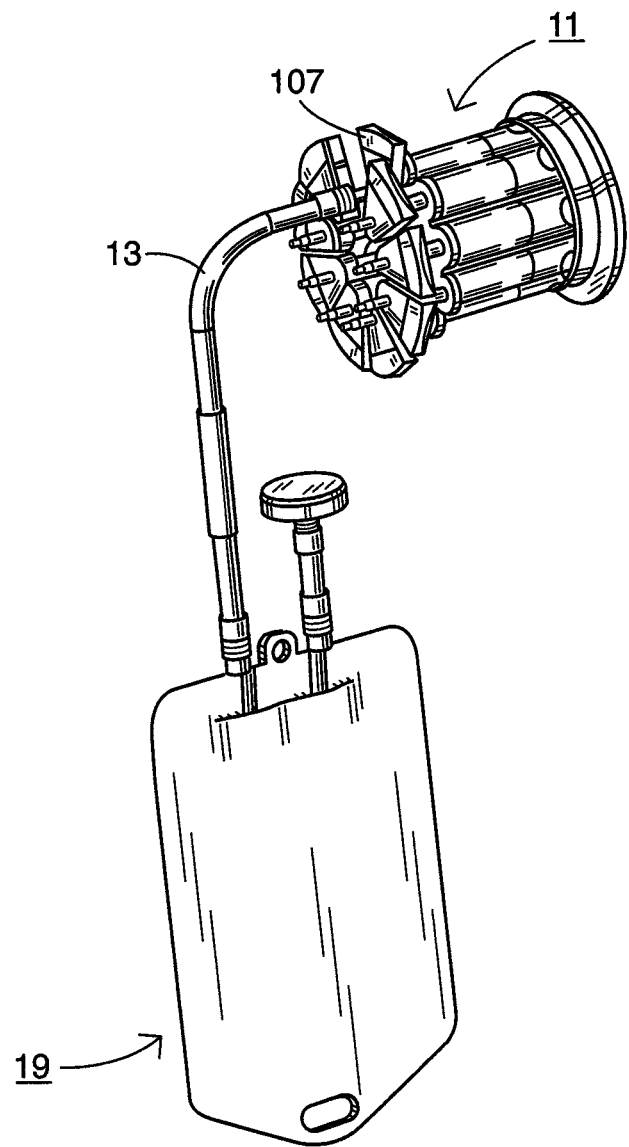

FIGS. 51A, 51B, and 51C illustrate an assembled fluid transfer device 11 during actuation, that is, a tab 107 is shown on the fluid transfer device 11 in a depressed state. The fluid transfer device may be used in a manner depicted in FIG. 51A wherein a single sample container 19 is fluidly connected to the fluid transfer device by way of flexible tubing 13. In the embodiments shown in FIGS. 51A, 51B, and 51C, it is understood that the fluid transfer device contains multiple individual fluid transfer devices joined together to form a cartridge to facilitate multiple transfers. The fluid transfer device provided herein may also be a single transfer device or joined together to provide for multiple transfer capabilities. In a preferred embodiment, the fluid transfer device comprises nine individual fluid transfer devices joined together, such as that depicted in FIGS. 51A and 51B in a cartridge configuration.

FIG. 51C depicts a cross-section of an embodiment of a fluid transfer device 11. As illustrated, the fluid transfer device 11 is connected to flexible tubing 13 which, in turn, is connected to a bag insert 23. FIG. 51C depicts the bolt 71 securing the components of the fluid transfer device together.

Figure 52:
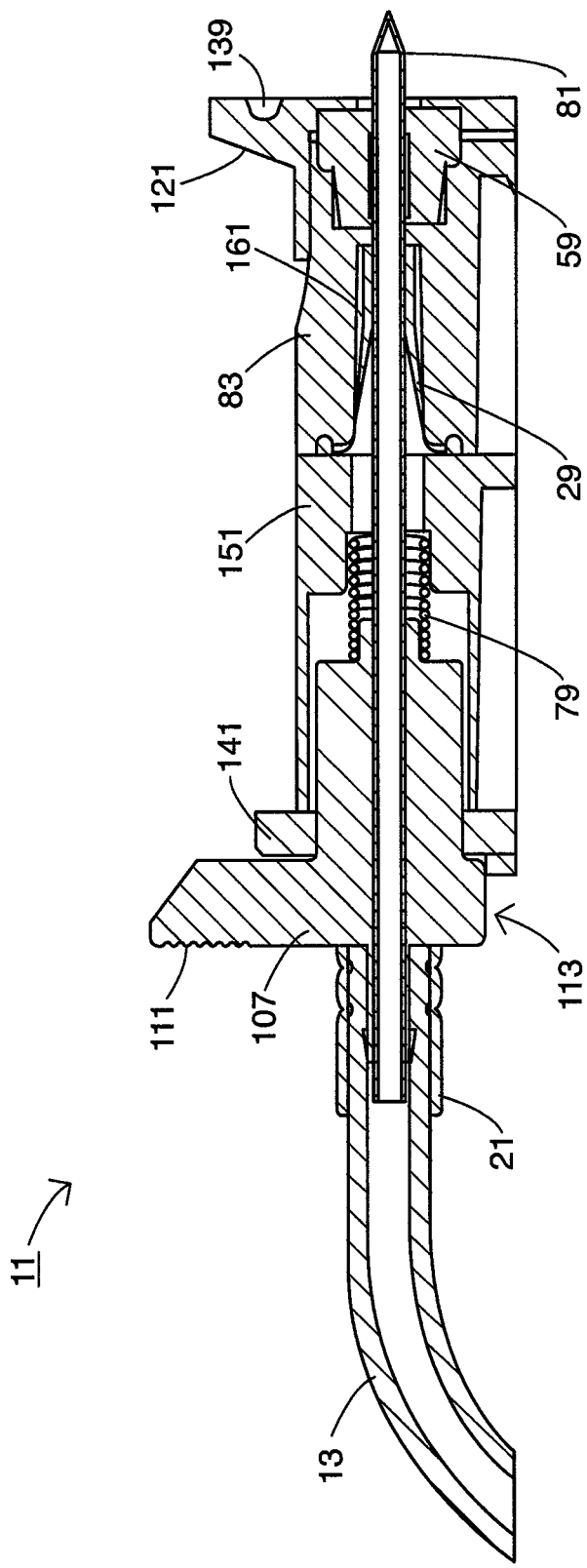
FIG. 52 is a cross-section of a fluid transfer device wherein the fluid transfer device is actuated.

Similar to FIG. 1, FIG. 52 illustrates in cross-section a preferred embodiment of a fluid transfer device 11 and illustrates how the majority of the various components described above operate together. However, unlike FIG. 1, as illustrated in FIG. 52, the fluid transfer device is shown during use, that is, with the cannula 81 extending through the septum 59. The fluid transfer device 11 comprises a tank mount 121 containing an annular groove 139. Also shown is the septum 59, a lower portion of the body 83, a diaphragm 29 (in a stretched state), an upper portion of the body 151, a spring 79, a retaining cap 141, a tab assembly 113, ridges 111 on the tab 107, a collar 21, and flexible tubing 13. The passage 161 comprises an elongated passage extending through the body of the fluid transfer device 11. The elongated passage has a proximal end and a distal end. In a preferred embodiment passage 161 is substantially aseptic and sealed from the environment. As discussed above, in a preferred embodiment, the cannula 81 is disposed in and longitudinally displaceable along the elongated passage with the tip of the cannula 81 disposed in the central cavity of the septum 59. As illustrated, a septum 59 seals the elongate passage at a proximal location. The septum 59 is both pierceable and self-sealing. Also illustrated is a diaphragm 29 that seals the elongate passage at a second, more distal location, from the septum 59. In this preferred embodiment, the portion of the elongate passage between the septum 59 and the diaphragm 29, and labeled as 161, is substantially aseptic and remains substantially aseptic during and after actuation. Upon actuation, the proximal end of the cannula may be drawn into passage 161. Because passage 161 is substantially aseptic and sealed from the environment, it prevents contamination of the fluid being transferred as well as contains any fluid that may flow out of the proximal end of cannula 81 during fluid transfer. FIG. 52 also depicts the cannula 81 extending through and being secured to the diaphragm 29. Thus when the cannula 81 is longitudinally displaced, the diaphragm 29 stretches to accommodate the resultant movement of the cannula 81 while maintaining a seal about the cannula. In a preferred embodiment, the fluid transfer device comes pre-sterilized. In yet another preferred embodiment, the entire passageway that fluid will travel is substantially aseptic until use. For example, and referring to FIG. 1, the tank mount 121, septum 59, cannula 81, passage 161, diaphragm 29, and flexible tubing 13 are all substantially aseptic. By rendering and maintaining the pathway that fluid travels substantially aseptic, the fluid may be transferred from one vessel to another with risk of contamination to the fluid.

Also provided is a kit containing a fluid transfer device 11 as described herein, that is, comprising one or more bodies joined together, one or more lengths of flexible tubing 13 as described herein, a plurality of sample containers 19 as described herein, and a tank mount 121 as described herein.

The fluid transfer device 11 may be assembled and then the entire device or components thereof may be rendered substantially aseptic by, for example, gamma radiation. In another embodiment, the entire device or components thereof may be rendered substantially aseptic by exposure to steam above 121° C. for a period of time long enough to eliminate microorganisms. In yet another embodiment, the entire device or components thereof may be rendered aseptic by chemical treatment, such as with ethylene oxide (ETO). In a preferred embodiment, the entire device is rendered substantially aseptic by gamma radiation. Once rendered substantially aseptic, the device may be appropriately packaged and stored to maintain the substantially aseptic state until ready for use.

All dimensional information presented herein and included in the drawings is intended to be illustrative and not intended to limit the scope of the invention.

The foregoing descriptions of fluid transfer devices illustrate and describe various embodiments considered to represent best modes of carrying out the invention. As various changes can be made in the above embodiments without departing from the scope of the fluid transfer device disclosed and claimed herein, it is intended that all matter contained in the above description or shown in the accompanying drawings shall be interpreted as illustrative and not limiting. Furthermore, the scope of the invention covers various modifications, combinations, alterations, etc., of the above-described embodiments that all are within the scope of the claims. Additionally, the disclosure shows and describes only selected embodiments of the invention, but the invention is capable of use in various other combinations, modifications, and environments and is capable of changes or modifications within the scope of the inventive concept as expressed herein, commensurate with the above teachings, and/or within the skill or knowledge of artisans in the relevant art. Furthermore, certain features and characteristics of each embodiment may be selectively interchanged and applied to other illustrated and non-illustrated embodiments of the invention without departing from the scope of the invention.

What is claimed is:

1. A fluid transfer device comprising:
    a body:
    an elongate passage extending through the body and having a proximal end and a distal end;
    a longitudinally displaceable cannula disposed in and extending along the passage;
    a septum sealing the passage at a first location, the septum being pierceable and self-sealing;
    a diaphragm sealing the passage at a second location intermediate the septum and the distal end of the passage;
    the cannula extending through and being secured to the diaphragm and having a sharpened end disposed adjacent the septum; and
    wherein longitudinal displacement of the cannula towards the septum causes its sharpened end to pierce and project through the septum, the diaphragm stretching to accommodate the displacement of the cannula while maintaining a seal about the cannula.

2. The device of claim 1 wherein the portion of the passage between the septum and diaphragm is substantially aseptic.

3. The device of claim 1, further comprising a tank mount.

4. The device of claim 3, wherein the fluid transfer device and tank mount are substantially aseptic.

5. The device of claim 3, wherein the tank mount defines an opening, the cannula passing through the opening when displaced.

6. The device of claim 3, further comprising a groove located in the tank mount and a seal recessed in the groove for forming a seal between the tank mount and a tank.

7. The device of claim 3, wherein the tank mount further comprises a threaded stud for mounting the fluid transfer device to a tank.

8. The device of claim 1, wherein a proximal end of the cannula is disposed in the septum prior to displacement.

9. The device of claim 1, wherein the diaphragm is constructed of a silicone elastomer.

10. The device of claim 1, wherein the septum is constructed of a silicone elastomer.

11. The device of claim 1, wherein the diaphragm is constructed of a solvent resistant elastomer.

12. The device of claim 11, wherein the diaphragm is constructed of a perfluoropolyether elastomer.

13. The device of claim 1, wherein the septum is constructed of a solvent resistant elastomer.

14. The device of claim 13, wherein the septum is constructed of a perfluoropolyether elastomer.

15. The device of claim 1, further comprising a tab assembly to which the cannula is connected, the tab assembly controlling the displacement of the cannula through the passage.

16. The device of claim 15, wherein a distal end of the tab assembly further comprises a barb.

17. The device of claim 15, wherein the tab assembly further comprises a tab guide, wherein longitudinal displacement of the tab assembly displaces the tab guide through a portion of the passage.

18. The device of claim 17, further comprising a retaining cap at a distal end of the body.

19. The device of claim 18, wherein the retaining cap comprises an opening through which the cannula and tab guide pass.

20. The device of claim 19, wherein the retaining cap engages a distal end of the body and further comprises restraining means to allow the tab guide and the cannula to move through the retaining cap and stop at a predetermined position.

21. The device of claim 20, wherein the restraining means comprises an axial channel extending along the tab guide and a detent extending from the opening in the retaining cap into the axial channel, whereby the detent limits longitudinal displacement of the tab guide so as to limit a range of movement of the tab guide.

22. The device of claim 1, wherein the cannula is axially biased longitudinally to maintain a proximal end of the cannula disposed adjacent the septum, and for retracting the cannula to a retracted non-actuated position after displacement.

23. The device of claim 22, wherein the cannula is axially biased by a spring.

24. The device of claim 1, wherein the body comprises a substantially cylindrical outer portion, at least one alignment aperture, and seats for the diaphragm and septum.

25. The device of claim 1, joined together with additional devices as described in claim 1 to form a cartridge having a plurality of bodies.

26. The device of claim 1, further comprising a safety retention band for preventing the cannula from longitudinal displacement.

27. The device of claim 1, further comprising a luer connected to a distal end of the cannula.

28. A fluid transfer device comprising:
    a plurality of bodies joined together, each body comprising:
    an elongate passage extending through the body and having a proximal end and a distal end;
    a longitudinally displaceable cannula disposed in and extending along the passage;
    a septum sealing the passage at a first location, the septum being pierceable and self-sealing;
    a diaphragm sealing the passage at a second location intermediate the septum and the distal end of the passage;
    the cannula extending through and being secured to the diaphragm and having a sharpened end disposed adjacent the septum; and
    wherein longitudinal displacement of the cannula towards the septum causes its sharpened end to pierce and project through the septum, the diaphragm stretching to accommodate the displacement of the cannula while maintaining a seal about the cannula.

29. A kit for transferring fluid comprising:
    a fluid transfer device comprising:
        one or more bodies joined together, each body comprising:
        an elongate passage extending through the body, each having a proximal end and a distal end;
        a longitudinally displaceable cannula disposed in and extending along the passage;
        a septum sealing the passage at a first location, the septum being pierceable and self-sealing;

a diaphragm sealing the passage at a second location intermediate the septum and the distal end of each passage;

the cannula extending through and being secured to the diaphragm and having a sharpened end disposed adjacent the septum;

wherein longitudinal displacement of the cannula toward the septum causes its sharpened end to pierce and project through the septum, the diaphragm stretching to accommodate the displacement of a cannula while maintaining its seal about the cannula;

a tank mount;

one or more lengths of flexible tubing; and a plurality of sample containers.

30. The kit of claim 29, wherein the fluid transfer device, tank mount, one or more lengths of flexible tubing, and plurality of sample containers are substantially aseptic.

* * * * *